United States Patent
Kwon et al.

(10) Patent No.: US 12,187,787 B2
(45) Date of Patent: Jan. 7, 2025

(54) ANTIBACTERIAL ANTIBODY AND USE THEREOF

(71) Applicant: INDUSTRY ACADEMIC COOPERATION FOUNDATION, HALLYM UNIVERSITY, Chuncheon-Si (KR)

(72) Inventors: Hyung Joo Kwon, Cheongju-Si (KR); Te Ha Kim, Chuncheon-Si (KR); Dong Bum Kim, Chuncheon-Si (KR)

(73) Assignee: INDUSTRY ACADEMIC COOPERATION FOUNDATION, HALLYM UNIVERSITY, Chuncheon-Si (KR)

( * ) Notice: Subject to any disclaimer, the term of this patent is extended or adjusted under 35 U.S.C. 154(b) by 1142 days.

(21) Appl. No.: 16/982,575

(22) PCT Filed: Feb. 26, 2019

(86) PCT No.: PCT/KR2019/002302
§ 371 (c)(1),
(2) Date: Sep. 20, 2020

(87) PCT Pub. No.: WO2019/182257
PCT Pub. Date: Sep. 26, 2019

(65) Prior Publication Data
US 2021/0017258 A1 Jan. 21, 2021

(30) Foreign Application Priority Data
Mar. 23, 2018 (KR) .................. 10-2018-0033849

(51) Int. Cl.
*C07K 16/12* (2006.01)
*A61K 39/00* (2006.01)
*A61P 31/04* (2006.01)

(52) U.S. Cl.
CPC .......... *C07K 16/1271* (2013.01); *A61K 39/00* (2013.01); *A61P 31/04* (2018.01); *C07K 16/12* (2013.01); *C07K 16/1232* (2013.01); *A61K 2039/505* (2013.01); *C07K 2317/24* (2013.01); *C07K 2317/565* (2013.01); *C07K 2317/622* (2013.01); *C07K 2317/73* (2013.01)

(58) Field of Classification Search
None
See application file for complete search history.

(56) References Cited

U.S. PATENT DOCUMENTS 10,113,003 B2 * 10/2018 Gauthier ............... A61P 37/06
2008/0025944 A1 * 1/2008 Hoerr ................... A61P 35/00
424/85.5

* cited by examiner

*Primary Examiner* — Ilia I Ouspenski

(57) ABSTRACT

The present invention relates to in a monoclonal antibody produced by CpG-DNA, or a functional fragment thereof, the monoclonal antibody, or functional fragment thereof, characterized in that it comprises polypeptide sequence selected from the group consisting of the following polypeptide sequences a heavy chain comprising a complementarity determining region 1 (CDR 1) amino acid sequence consisting of the sequence of SEQ ID NO: 1, a CDR2 consisting of the sequence of SEQ ID NO: 2 and a CDR 3 consisting of the sequence of SEQ ID NO: 3; and a light chain comprising CDR1 amino acid sequence consisting of the sequence of SEQ ID NO: 4, a CDR2 consisting of the sequence of SEQ ID NO: 5 and a CDR 3 consisting of the sequence of SEQ ID NO: 6 and a use of the same.

5 Claims, 18 Drawing Sheets
Specification includes a Sequence Listing.

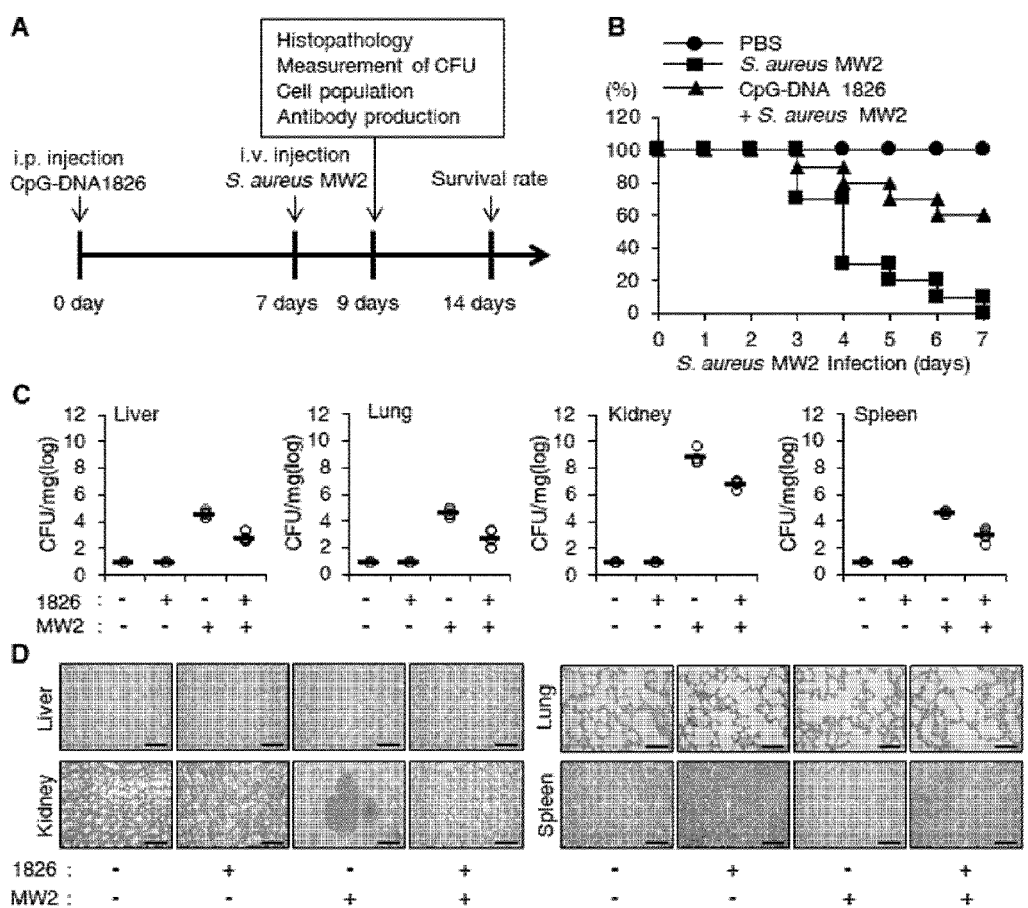
[Fig. 1]

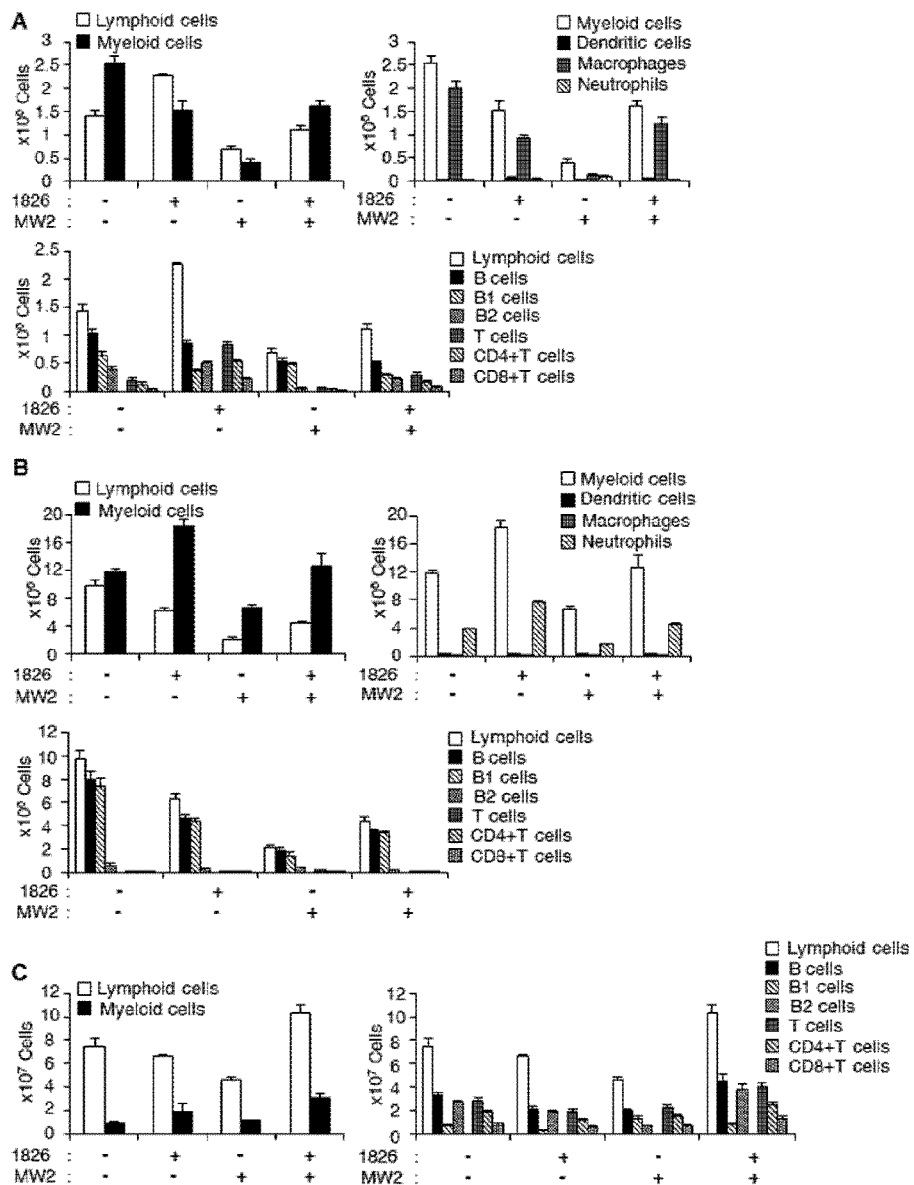
[Fig. 2]

[Fig. 3]
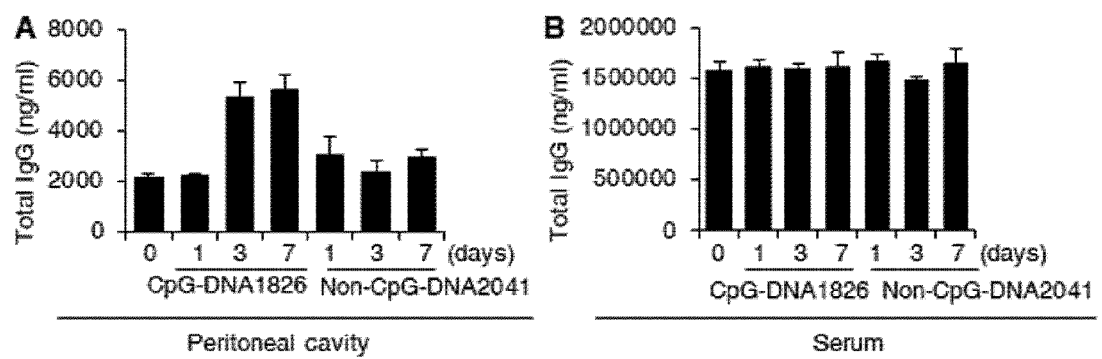

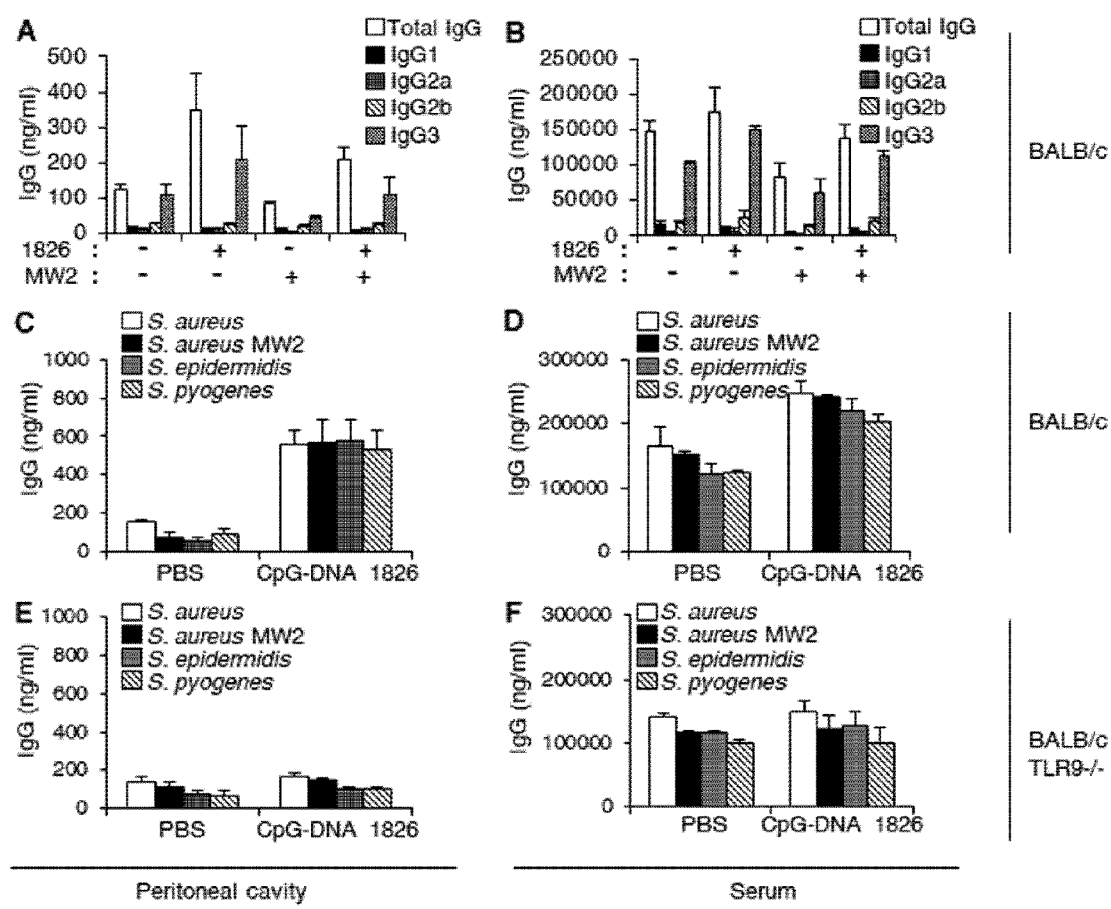
[Fig. 4]

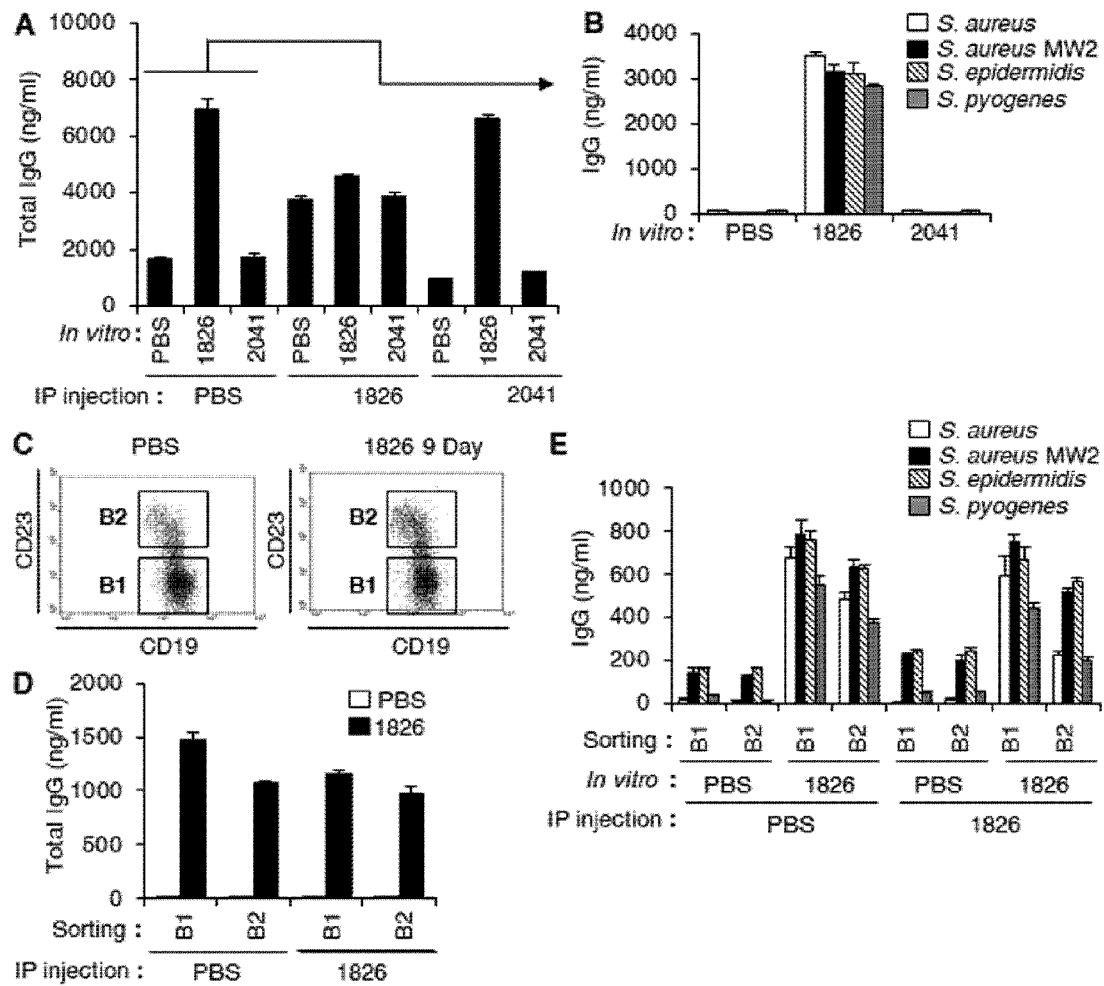
[Fig. 5]

[Fig. 6]
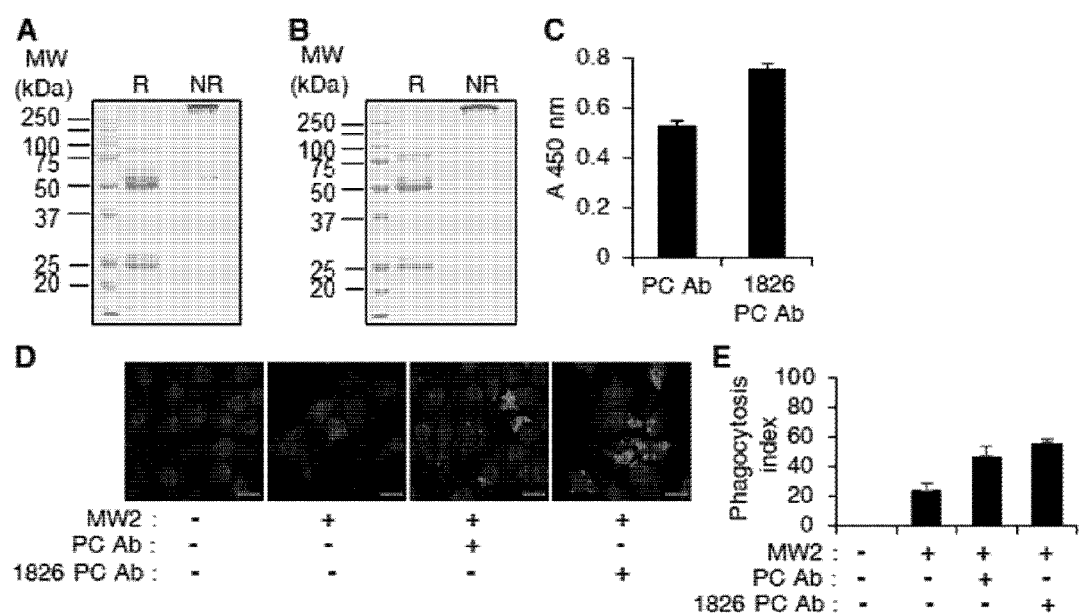

[Fig. 7]
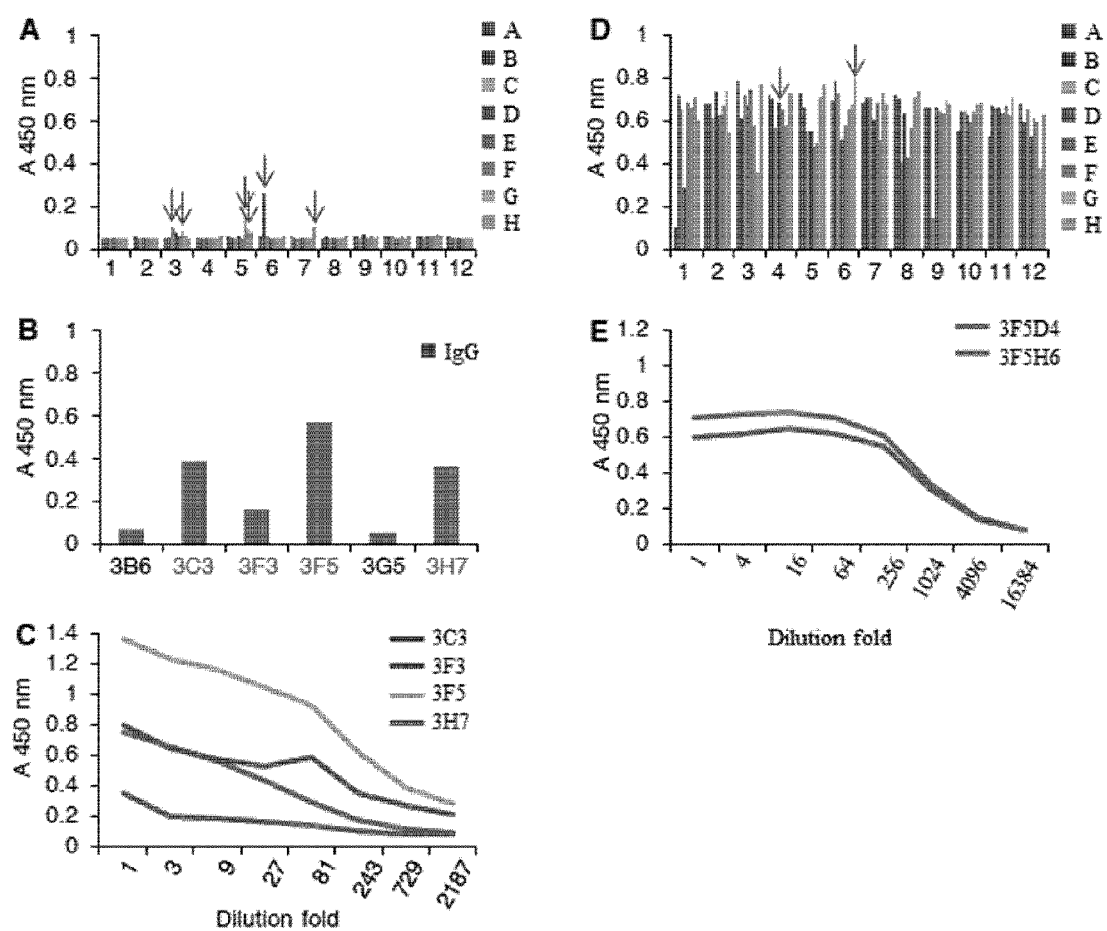

[Fig. 8]

Heavy chain

GAGGTCCAGCTGCAACAGTCTGGACCTGAGCTGGTGAAGCCTGGGGCTTCAGTGAAGATATCCTGCAAGGCTTCTGGTTA
CTCATTCACTGGCTACTACATGCACTGGGTGAAGCAAAGCCATGTAAAGAGCCTTGAGTGGATTGGACGTATTAATCCTT
ACAATGGTGCTACTAGCTACAACCAGAATTTCAAGGACAAGGCCAGCTTGACTGTAGATAAGTCCTCCAGCACAGCCTAC
ATGGAGCTCCACAGCCTGACATCTGAGGACTCTGCAGTCTATTACTGTGCAGGGGACTACGGTAGTAGCTACTTTGACTA
CTGGGGCCAAGGCACCACTCTCACAGTCTCCTCA

```
                         CDR1                          CDR2
Kabat                   <---->            <--------------->
AbM                   <-------->           <---------->
Chothia               <------>                <---->
EVQLQQSGPELVKPGASVKISCKAS GYSFTGYYMH WVKQSHVKSLEWIG RINPYNGATSYNQNFKD KASLTVDKSSSTAY CDR3
Kabat       <-------->
AbM         <-------->
Chothia     <-------->
MELHSLTSEDSAVYYCAG DYGSSYFDY WGQGTTLTVSS
```

Light chain

GACATTGTGATGACTCAGTCTCCAGCCACCCTGTCTGTGACTCCAGGAGATAGAGTCTCTCTTTCCTGCAGGGCCAGCCA
GAGTATTAGCGACTACTTACACTGGTATCAACAAAAATCACATGAGTCTCCAAGGCTTCTCATCAAATATGCTTCCCAAT
CCATCTCTGGGATCCCCTCCAGGTTCAGTGGCAGTGGATCAGGGTCAGATTTCACTCTCAGTATCAACAGTGTGGAACCT
GAAGATGTTGGAGTGTATTACTGTCAAAATGGTCACAGCTTTCCGCTCACGTTCGGTGCTGGGACCAAGCTGGAGCTGAA
ACGG

```
                      CDR1                     CDR2
                <---------->              <------>
DIVMTQSPATLSVTPGDRVSLSC RASQSISDYLH WYQQKSHESPRLLIK YASQSIS GIPSRFSGSGSGSDFTLSINSVEP

CDR3
       <-------->
EDVGVYYC QNGHSFPLT FGAGTKLELKR
```

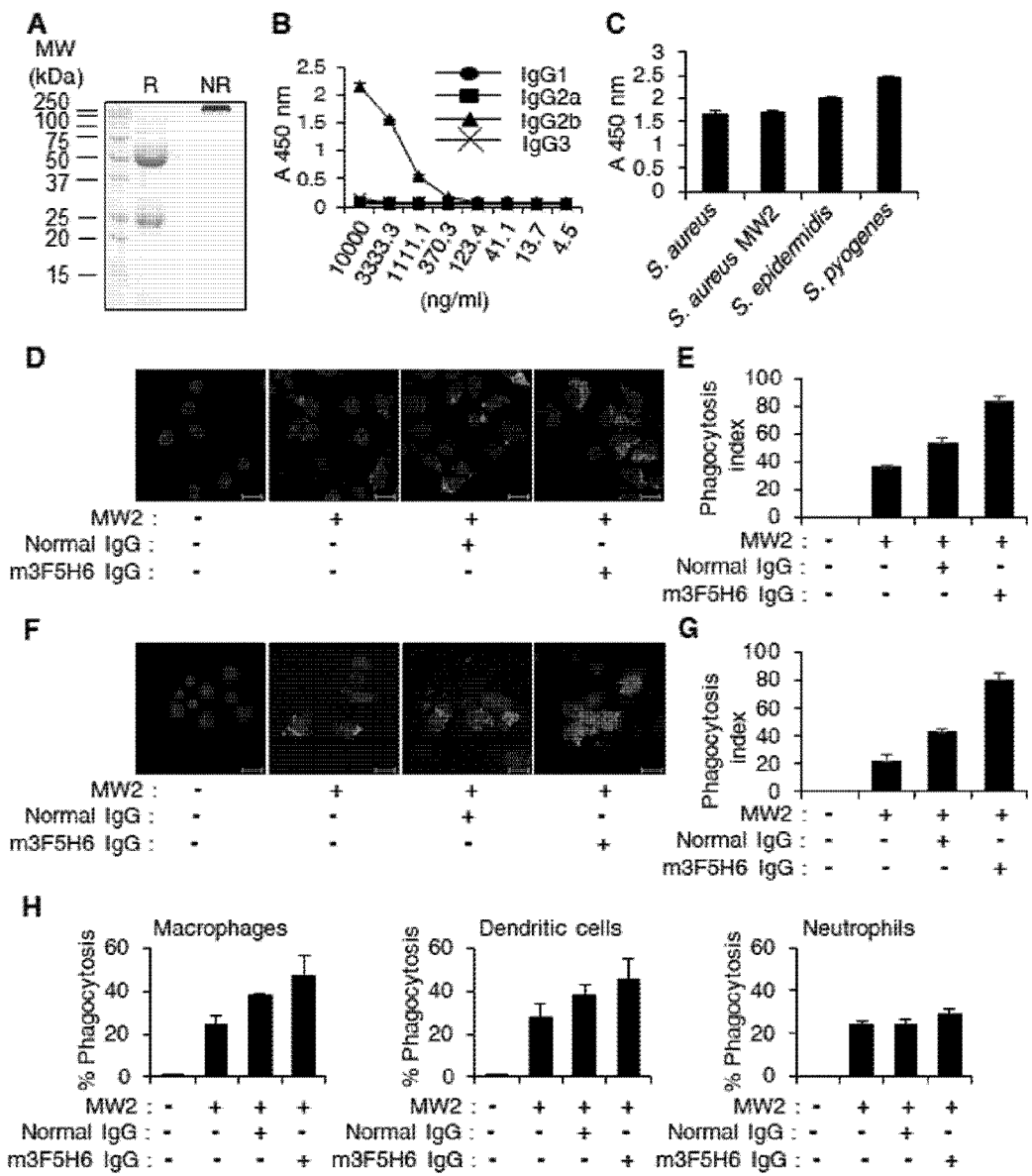
[Fig. 9]

[Fig. 10]
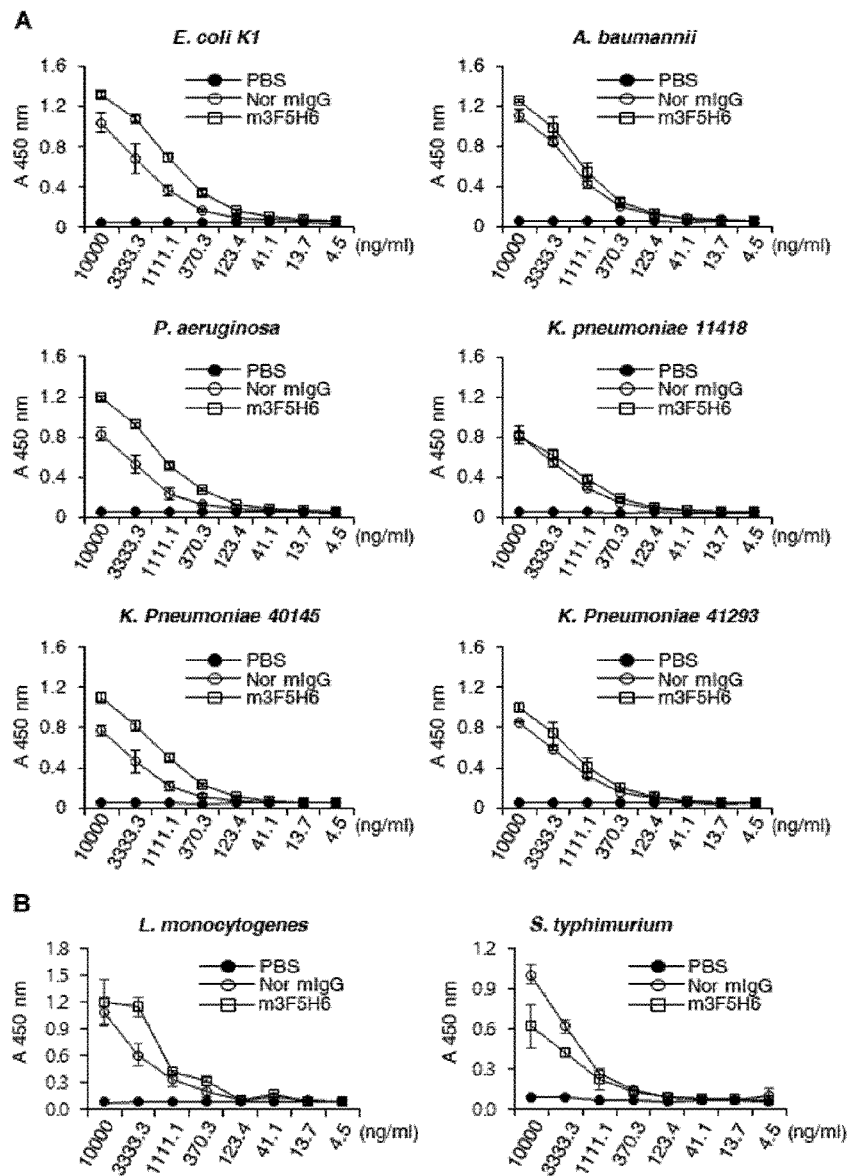

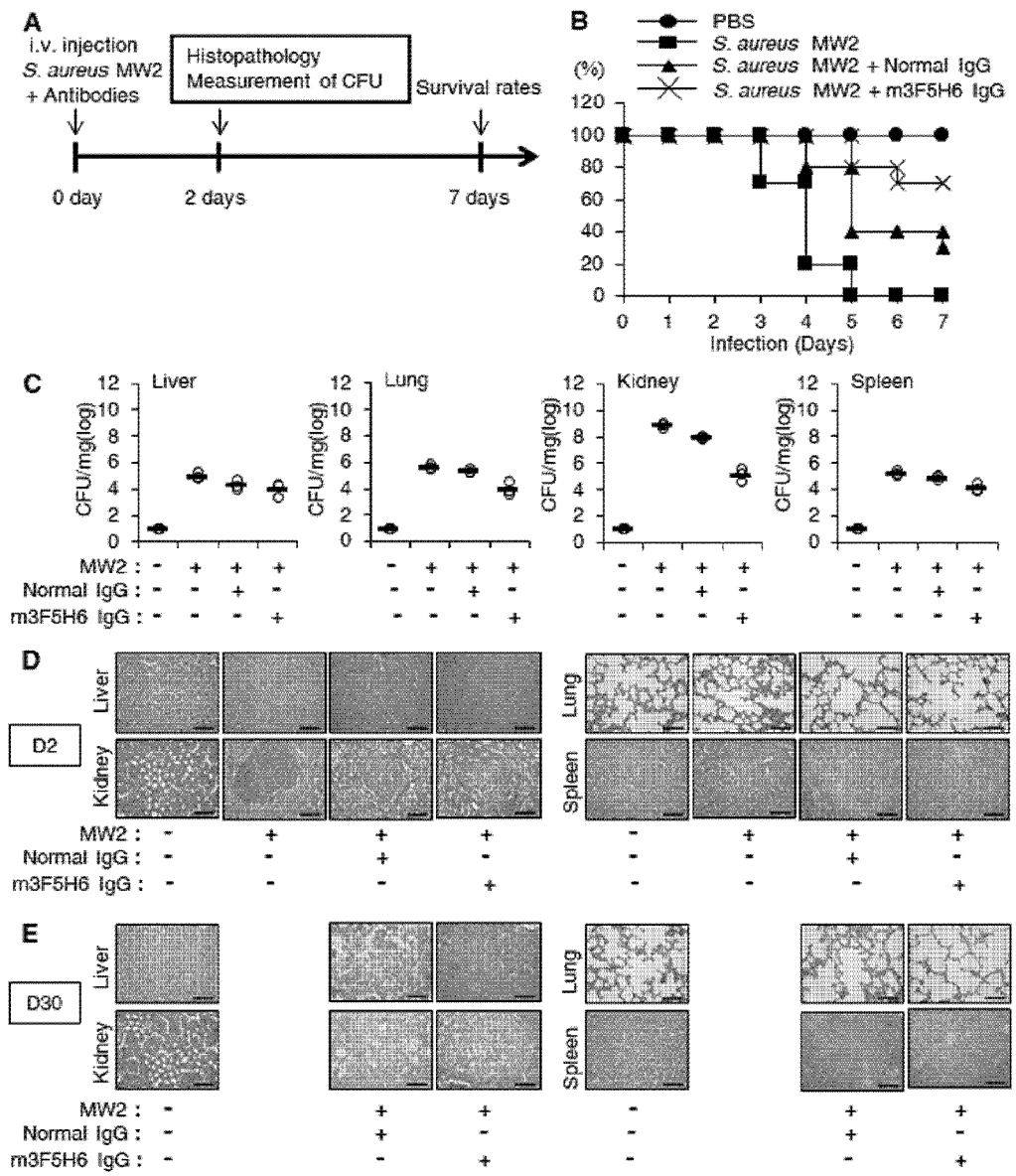
[Fig. 11]

```
              10          20          30          40          50          60
m3F5H6   EVQLQQSGPELVKPGASVKISCKAS [GYSFTGYYMH] WVKQSHVKSLEWIG [RINPYNGATSY
hVH1     QVQLQQSGSELKKPGASVKISCKAS [GYSFTDYIIL] WVRQNPGKGLEWIG [HIDPYYGSSNY
h3F5H6   QVQLQQSGPELVKPGASVKISCKAS [GYSFTGYYMH] WVRQNHVKGLEWIG [RINPYNGATSY
          ▲ ▲                                                  ▲▲

70          80          90          100         110
m3F5H6   NQNFKD] KASLTVDKSSSTAYMELHSLTSEDSAVYYCAG [DYGSSYFDY] WGQGTTLTVSS
hVH1     NLKFKG] RVTITADQSTTTAYMELSSLRSEDTAVYYCGR [-SKRDYFDY] WGQGTTLTVSS
h3F5H6   NQNFKD] RATLTVDKSTTTAYMELHSLTSEDTAVYYCAG [DYGSSYFDY] WGQGTTLTVSS
                 * * * *            ▲ ▲          **
```

VL

```
              10          20          30          40          50
m3F5H6   DIVMTQSPATLSVTPGDRVSLSC [RASQSISDYLH] WYQQKSHESPRLLIK [YASQSIS]
hVk1     DIQMTQSPSSLSASIGDRVTITC [KASQDINSYLS] WFQQKPGKAPKLLIY [RANRLVD]
h3F5H6   DIVMTQSPSSLSASPGDRVTITC [RASQSISDYLH] WYQQKSHKAPKLLIK [YASQSIS]
           ▲             ▲                             * ▲▲        *
              60          70          80          90          100
m3F5H6   GIPSRFSGSGSGSDFTLSINSVEPEDVGVYYC [QNGHSFPLT] FGAGTKLELKR
hVk1     GVPSRFSGSGSGTDYTLTISSLQPEDFAVYYC [LQYDEFPYT] FGGGTKLEIKR
h3F5H6   GVPSRFSGSGSGSDYTLTISSLQPEDFAVYYC [QNGHSFPLT] FGGGTKLEIKR
                       *
```

[Fig. 13]

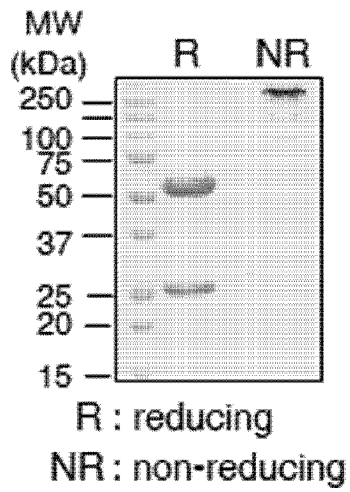

R : reducing
NR : non-reducing

[Fig. 14]
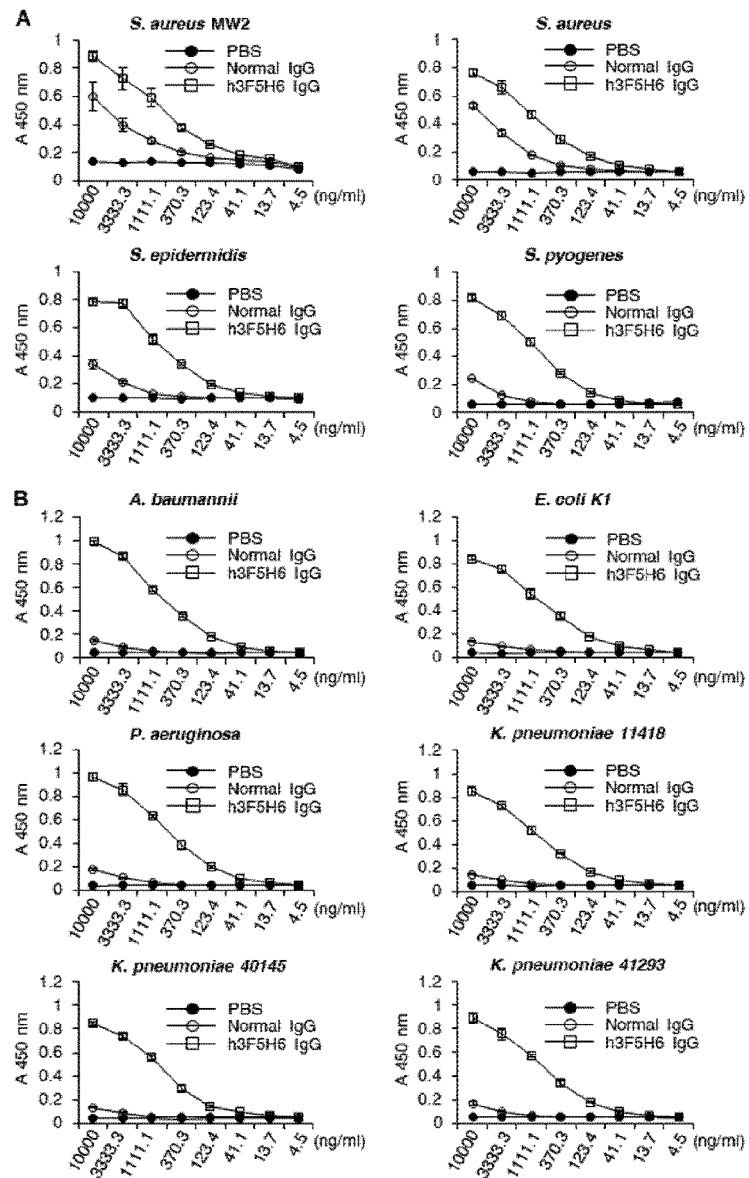

[Fig. 15]
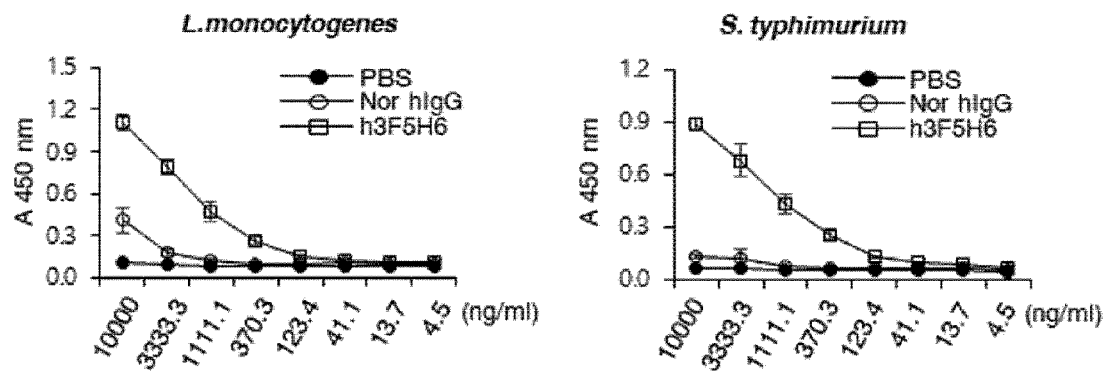
[Fig. 16]
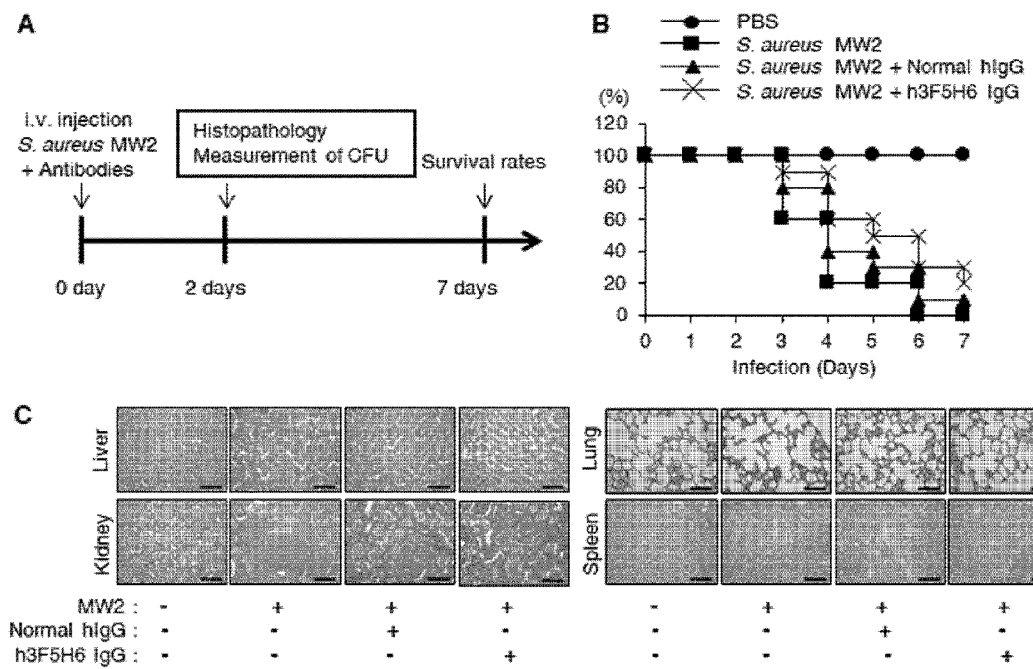

[Fig. 17]
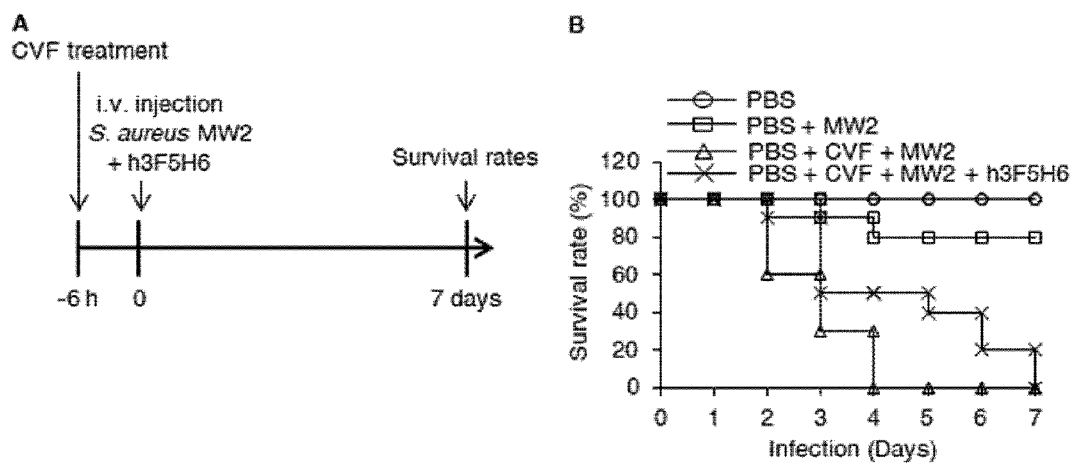

[Fig. 18]
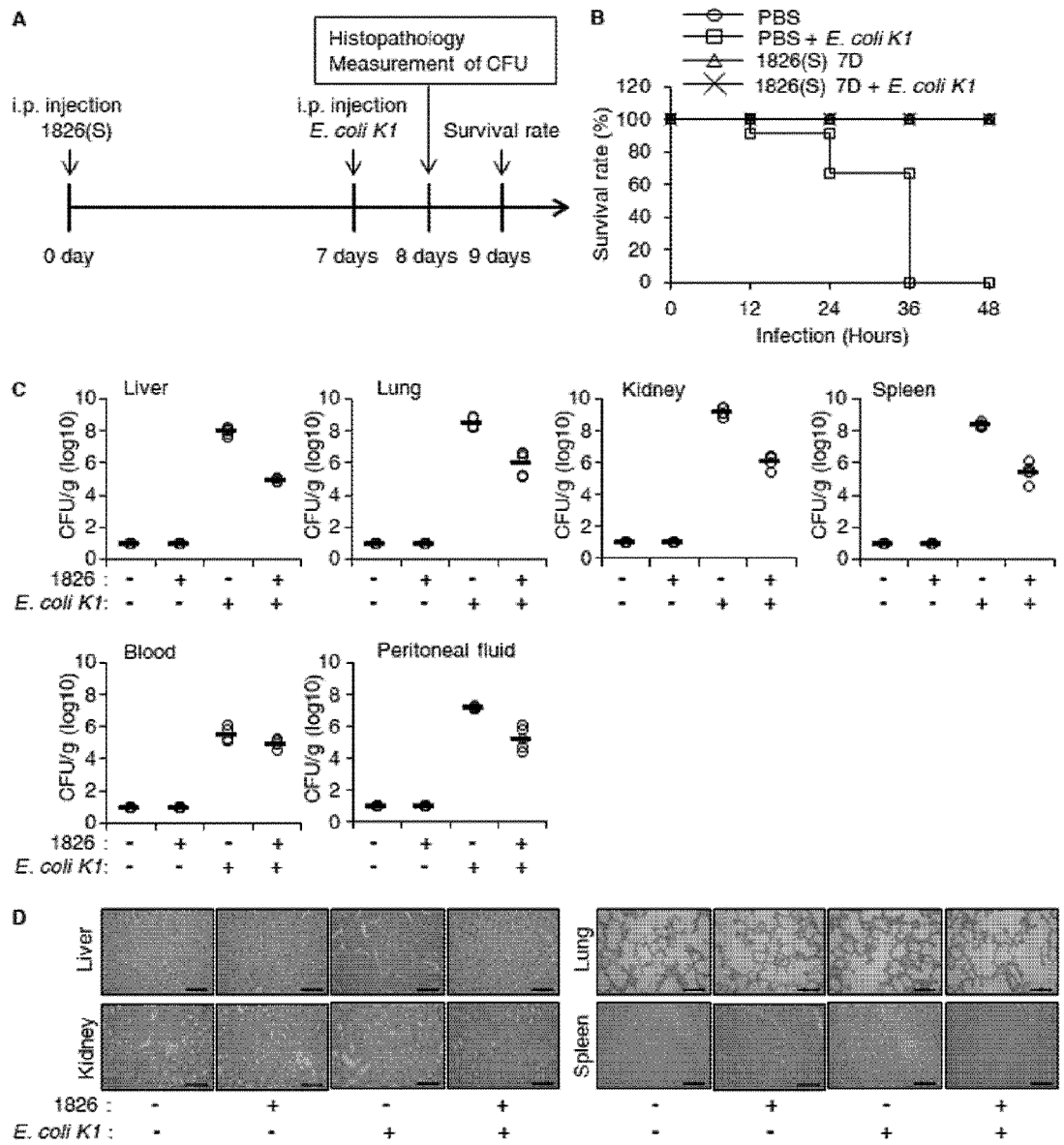

【Fig. 19】
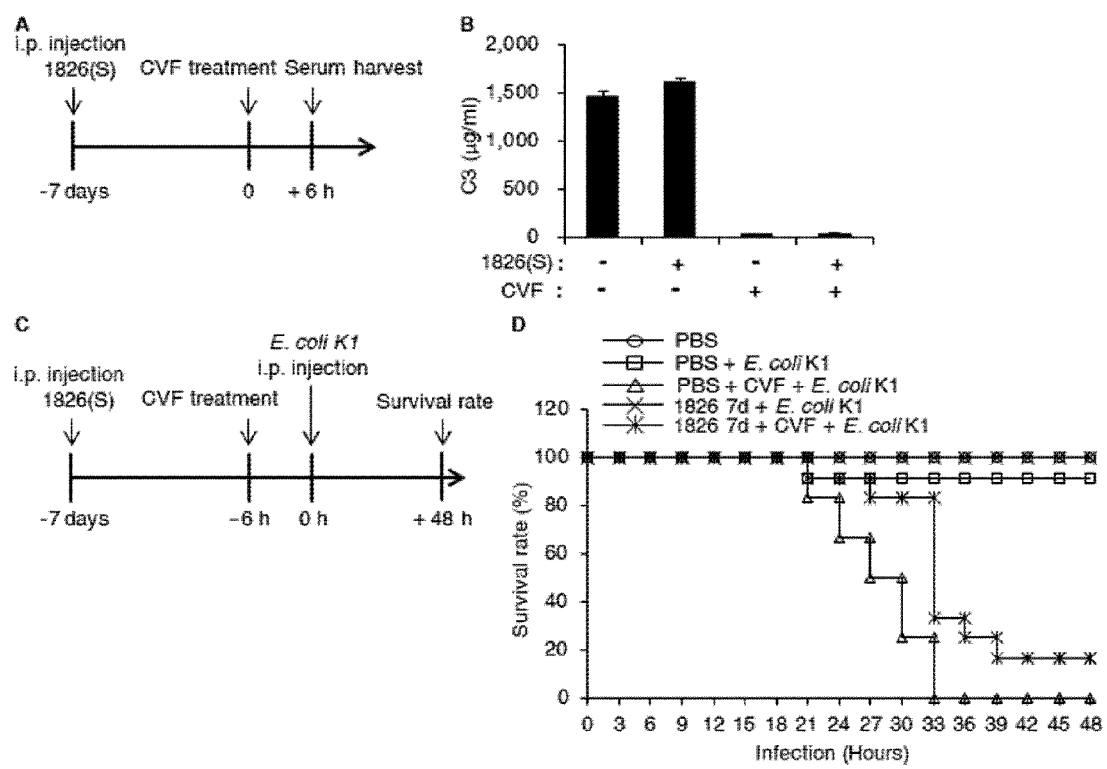

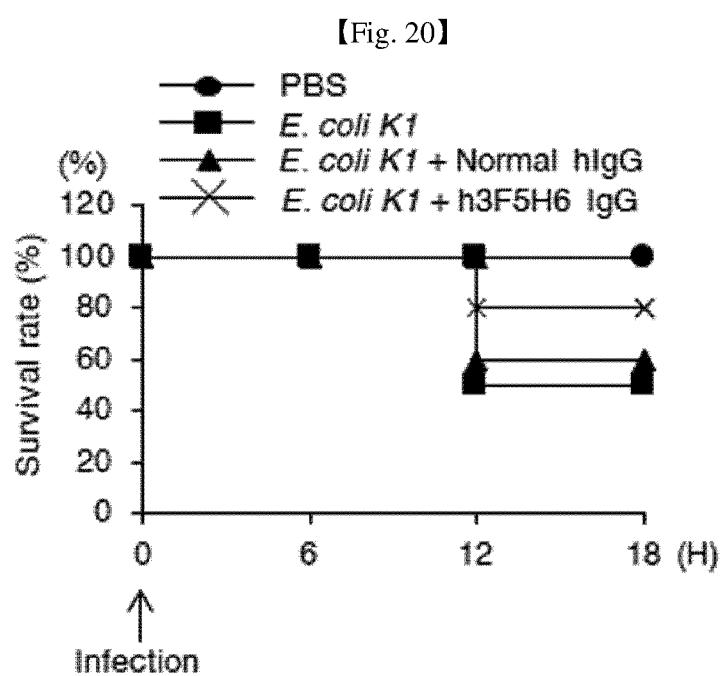
[Fig. 20]

ANTIBACTERIAL ANTIBODY AND USE THEREOF

TECHNICAL FIELD

The present invention relates to antibacterial antibodies and uses thereof.

BACKGROUND ART

The innate immune system is the first defense line against invading pathogens and potentially harmful agents to the host. The recognition of pathogens depends on the conserved structures known as pathogen-associated molecular patterns (PAMPs) via pattern recognition receptors (PRRs) in the innate immune cells. Toll-like receptors (TLRs) are the major and widely-studied PRRs, and the activation of TLRs induce immune responses, producing cytokines, chemokines, and various immune cells, which subsequently defend against pathogens, such as bacteria, viruses, and parasites.

Toll-like receptor 9 (TLR9) is the well-known receptor to detect bacterial DNA, leading to immunomodulatory effects in the host. Bacterial DNA and synthetic oligonucleotides that contain CpG dinucleotide motifs (CpG-DNA) activate various cells to proliferate and produce However, the antibody produced by CpG-DNA stimulation and its action are unknown.

Methicillin-resistant *Staphylococcus aureus* (MRSA) is the main reason of interest for clinicians dealing with direct patients, and it exhibits a higher mortality and incidence than infections caused by methicillin-sensitive *staphylococcus*. In addition, these infections result in higher costs with longer hospitalization times and antimicrobial agents, resulting in significantly higher costs for the treatment of patients infected by these pathogens.

Vancomycin was the first antimicrobial agent of choice for the treatment of infections caused by MRSA. The content of the resistance of MRSA strains to vancomycin in 2004 has raised tremendous concern in the medical-scientific community. Currently, MRSA represents the most potent candidate for the fearsome "superbug or super-bacteria", a pathogen that is resistant to all drugs currently available.

Typically, the prevalence of MRSA (the proportion of *Staphylococcus aureus* caused by MRSA among all infections) in nosocomial infections has been increasing gradually over the past few decades. In a study conducted by Jarvis et al., including 1268 ICUs (Intensive Care Units) in 337 hospitals in the United States, the number of infections caused by MRSA in the ICU changed from 660 to 2184, and the prevalence was also increased 35%. to 64.4%. In Japan, the prevalence of hospital infections (HIs) caused by MRSA ranges from 60% to 90% of concern. In a study conducted in the United States, the percentile changed from 2% in 1974 to 50% in 1997.

MRSA strains provide penicillin-binding proteins with very low affinity for antimicrobial agents in the beta-lactam class such as PBP2a. In the presence of this enzyme encoded by the gene mecA, bacteria successfully synthesize peptide glycans, even in the presence of beta-lactam. In addition to resistance to beta-lactam, pathogenic MRSA strains also exhibit resistance to other available antimicrobial classes, with the use of glycopeptides (vancomycin and teicoplanin), which is the first choice for treatment.

Two studies using DNA vaccines against PBP2a have shown that these proteins are immunogenic, and that the acquired immune response could confer defense against MRSA in studies conducted in a mouse model. However, for nosocomial infections, most patients are known to be immune suppressed. In this case, the vaccine will not be able to produce protective antibodies within a reasonable time to control bacterial infection.

PRIOR ART DOCUMENT

Korean Patent Publication No. 10-2010-0108428

DISCLOSURE

Technical Problem

An object of the present invention is to provide an antibody produced by CpG-DNA stimulation. Another object of the present invention is to provide the use of an antibody produced by CpG-DNA stimulation.

Technical Solution

In order to achieve the above object, a monoclonal antibody produced by CpG-DNA, or a functional fragment thereof, according to an embodiment of the present invention comprises the monoclonal antibody, or functional fragment thereof, characterized in that it comprises polypeptide sequence selected from the group consisting of the following polypeptide sequences:
a heavy chain comprising a complementarity determining region 1 (CDR 1) amino acid sequence consisting of the sequence of SEQ ID NO: 1, a CDR2 consisting of the sequence of SEQ ID NO: 2 and a CDR 3 consisting of the sequence of SEQ ID NO: 3; and a light chain comprising CDR1 amino acid sequence consisting of the sequence of SEQ ID NO: 4, a CDR2 consisting of the sequence of SEQ ID NO: 5 and a CDR 3 consisting of the sequence of SEQ ID NO: 6.

According to an embodiment of the present invention, said functional fragment is preferable a single chain variable fragment (scFv); a Fab; a light chain or a heavy chain comprising the CDR region of the monoclonal antibody; or a variable domain comprising the CDR region of the monoclonal antibody, but is not limited thereto.

According to an embodiment of the present invention, said monoclonal antibody preferably comprises a heavy chain comprising an amino acid sequence consisting of the sequence of SEQ ID NO: 7, or the sequence of SEQ ID NO: 15; and a light chain comprising an amino acid sequence consisting of the sequence of SEQ ID NO: 8, or the sequence of SEQ ID NO: 16, but is not limited thereto.

According to an embodiment of the present invention, said CpG-DNA is preferable a base sequence consisting of the sequence of SEQ ID NO 9, but is not limited thereto.

In addition, the present invention provides an antibacterial composition comprising the monoclonal antibody of the present invention or a functional fragment thereof as an active ingredient.

According to an embodiment of the present invention, the composition preferably has antibacterial activity against Gram-positive bacteria, Gram-negative bacteria, intracellular parasitic bacteria, or drug-resistant bacteria, and the composition more preferably has antimicrobial activity against methicillin-resistant *Staphylococcus aureus* (MRSA), *Staphylococcus aureus, Listeria, Salmonella*, or *E. coli*, but is not limited thereto.

In addition, the present invention provides an antimicrobial composition comprising a monoclonal antibody produced by CpG-DNA, or a functional fragment thereof.

According to an embodiment of the present invention, the monoclonal antibody, or functional fragment thereof preferably comprises polypeptide sequence selected from the group consisting of the following polypeptide sequences: a heavy chain comprising a complementarity determining region 1 (CDR 1) amino acid sequence consisting of the sequence of SEQ ID NO: 1, a CDR2 consisting of the sequence of SEQ ID NO: 2 and a CDR 3 consisting of the sequence of SEQ ID NO: 3; and a light chain comprising CDR1 amino acid sequence consisting of the sequence of SEQ ID NO: 4, a CDR2 consisting of the sequence of SEQ ID NO: 5 and a CDR 3 consisting of the sequence of SEQ ID NO: 6, but is not limited thereto.

In addition, the present invention provides a method for producing an antibody having antibacterial activity against methicillin-resistant *Staphylococcus aureus* (MRSA), *staphylococcus*, *E. coli*, *Salmonella*, or *Listeria* by administering CpG-DNA to an animal.

The present invention will be described below.

In this invention, we propose a novel function of CpG-DNA in the context of production of bacteria-reactive antibodies. Administration of CpG-DNA enhanced survival of mice after infection with methicillin-resistant *S. aureus* MW2 and facilitated bacterial clearance in tissues of mice. CpG-DNA administration alone modulated immune cell population especially in peritoneal cavity in a direction to increase adaptive immunity. While infection of *S. aureus* MW2 induced drastic decrease of total cell numbers in the peritoneal cavity, bone marrow, and spleen, pretreatment of the mice with CpG-DNA commonly protected immune cell populations. Injection of mice with CpG-DNA induced increase of bacteria-reactive antibodies, which can bind with diverse species of bacteria, in the peritoneal cavity and serum through TLR9-dependent pathway. Stimulation of peritoneal cavity cells with CpG-DNA induced bacteria-reactive antibodies in vitro. The bacteria-reactive antibodies were produced in both B1 and B2 cells of peritoneal cavity in response to CpG-DNA, and the antibodies enhanced phagocytosis in the peritoneal cavity of mice. A hybridoma clone producing bacteria-reactive monoclonal antibody was selected from CpG-DNA stimulated-peritoneal B cells. We established a monoclonal antibody reactive to bacteria and humanized the antibody sequence by CDR grafting into stable human framework. The purified monoclonal antibody was reactive to various bacteria and enhanced phagocytosis of *S. aureus* MW2 in a macrophage cell line and the primary peritoneal cavity cells. Injection with the bacteria-reactive monoclonal antibody had therapeutic effects after infection of *S. aureus* MW2 with enhanced survival rate and bacterial clearance. The purified bacteria-reactive humanized monoclonal antibody (h3F5H6 IgG) was reactive to various bacteria (G(+) and G(−) bacteria) and injection with the humanized bacteria-reactive antibody had therapeutic effects after infection of *S. aureus* MW2 and *E. coli* K1 with enhanced survival rate and bacterial clearance. Therefore, we suggest that CpG-DNA enhances anti-bacterial activity of immune system by generally protecting immune cell population and also by inducing production of bacteria-reactive antibodies in the peritoneal cavity. We also suggest the utility of the isolated the monoclonal antibody and humanized monoclonal antibody in treatment of urgent clinical situation caused by bacteria infection.

In addition, the present invention provides a pharmaceutical composition containing the antibody or single chain variable fragment (scFv) of the present invention as an active ingredient.

Further, the present invention provides a composition for preventing or treating infection, comprising the antibody of the present invention or a single chain variable fragment (scFv) thereof as an active ingredient.

In addition, the present invention provides an anti-infective composition comprising the antibody of the present invention or a single chain variable fragment (scFv) thereof as an active ingredient.

The pharmaceutical composition of the present invention may further include pharmaceutically acceptable excipients, carriers, diluents, and the like.

Carriers that can be used in the present invention include proteins, polypeptides, liposomes, polysaccharides, polylactic acid, polyglycolic acid, polymeric amino acids, amino acid copolymers, and slowly metabolized macromolecules such as inactive virus particles. Salts of inorganic acids such as, for example, hydrochloride, hydrobromide, phosphate and sulfate; pharmaceutically acceptable salts such as salts of organic acids such as acetate, propionate, malonate and benzoate; liquids such as water, saline, glycerol and ethanol, and auxiliary substances such as wetting agents, emulsifiers or pH buffering substances can be used.

A pharmaceutically acceptable carrier is described in Remington's Pharmaceutical Sciences, Mack Publishing Company, 1991.

In addition, the composition is formulated in a unit dosage form suitable for intra-body administration of a patient according to a conventional method in the pharmaceutical field, preferably in the form of a preparation useful for administration of protein medicines, and administration commonly used in the art. It may be administered by an oral, or a parenteral route including intravenous, intramuscular, intraarterial, intramedullary, intramenal, intraventricular, pulmonary, transdermal, subcutaneous, intraperitoneal, intranasal, intestinal, local, sublingual, intravaginal or rectal routes, but is not limited thereto.

Formulations suitable for this purpose include various formulations for oral administration such as tablets, pills, dragees, powders, capsules, syrups, solutions, gels, suspensions, emulsions, and microemulsions; and preparations for parenteral administration such as injections such as ampoules for injection, infusions, and sprays such as hypospray. Formulations for injection or infusion may take the form of a suspension, solution, or emulsion, and may include formulation agents such as suspending, preserving, stabilizing and/or dispersing agents. In addition, the antibody molecule may be formulated in a dried form that can be readjusted to an appropriate sterile liquid before use.

Since the composition of the present invention contains an antibody molecule that is easily degraded in the gastrointestinal tract as an active ingredient, when the composition is to be administered by a route using the gastrointestinal tract, it is preferable to include a drug that protects the antibody from degradation and is absorbed into the gastrointestinal tract after releasing the antibody.

The present invention also provides a method for preventing or treating an infectious disease comprising administering the antibody of the present invention to an animal, preferably a mammal, and more preferably a human, by various methods as described above.

As an active ingredient of the composition or pharmaceutical formulation of the present invention, the antibody can be administered to mammals including humans one or several times with 0.001 to 50 mg/kg body weight, preferably 0.1 to 20 mg/kg body weight per day. However, It is to be understood that the actual dosage of the active ingredient is to be determined in the light of various related factors such as the disease to be prevented or treated, the severity of the disease, the route of administration, the patient's weight, age and gender, the drug combination, sensitivity to reaction, and resistance/response to the treatment. and therefore, the above dosage is not in any way limiting the scope of the invention.

Functional antibody fragments of the present invention include light chain, heavy chain, variable region, Fab, Fab', F(ab')2, scFv, Diabody, Tribody, dsFv, and peptides containing CDRs.

Fab is a fragment obtained by treating IgG with the protease papain (cut to the 224th amino acid residue of the heavy chain), about half of the N-terminal side of the heavy chain and the whole light chain are bound by disulfide bonds (S—S bonds). It is an antibody fragment with antigen-binding activity having 50,000 Molecular weight.

The Fab of the present invention can be obtained by treating the antibody of the present invention with the protease papain. Alternatively, the DNA encoding the Fab of the antibody is inserted into a prokaryotic expression vector or an expression vector for eukaryotes, and the vector is introduced into a prokaryote or eukaryote to express it to prepare a Fab.

F(ab')2 is a fragment obtained by treating IgG with the protease pepsin (cut to the 234th amino acid residue in the heavy chain) and it is an antibody fragment having an antigen-binding activity of about 100,000 M. W. that Fab bound through the S—S bond of the hinge region F(ab')2 of the present invention can be obtained by treating the antibody of the present invention with the protease pepsin. Alternatively, it can be produced by preparing the following Fab' with thioether binding or S—S binding. Fab' is an antibody fragment having an antigen-binding activity of about 50,000 molecular weight by cleaving the S—S bond of the hinge region of F(ab')2.

scFv is a VH-P-VL or VL-P-VH polypeptide in which one VH and one VL are linked using a suitable peptide linker (P) of 12 or more residues, and is an antibody fragment having antigen-binding activity.

The scFv of the present invention obtains cDNA encoding VH and VL of the antibody of the present invention, constructs a DNA encoding scFv, and inserts the DNA into an expression vector for prokaryote or an expression vector for eukaryote to obtain the expression vector. It can be produced by expression by introduction into prokaryotes or eukaryotes.

Diabody is an antibody fragment in which scFvs having the same or different antigen-binding specificities form a dimer and is an antibody fragment having a bivalent antigen-binding activity for the same antigen or a bispecific antigen-binding activity for different antigens. Diabody of the present invention, for example, obtains cDNA encoding VH and VL of the antibody of the present invention, constructs a DNA encoding scFv having a polypeptide linker of 3 to 15 residues, and expresses the DNA for prokaryote By inserting into a vector or an expression vector for eukaryotes, the expression vector can be introduced into a prokaryote or eukaryote to express a Diabody.

In addition, when the linker P length is 3-10, a tribody is formed and may be included as a tribody.

dsFv refers to a polypeptide obtained by substituting a cysteine residue for one of the amino acid residues of VH and VL, which is bonded via an S—S bond between the cysteine residues. Amino acid residues substituted with cysteine residues can be selected based on prediction of the conformational structure of an antibody according to the method described by Reiter et al. (Protein Engineering, 7, 697 (1994)).

Effects of the Invention

As can be seen through the present invention, the antibody of the present invention promotes the antimicrobial activity of the immune system by protecting the immune cell population.

DESCRIPTION OF DRAWINGS

FIG. 1. CpG-DNA protects mice from *S. aureus* MW2 infection. (A) Schematic diagram of the experimental process. BALB/c mice were administered i.p. with CpG-DNA 1826. After 7 days, the mice were injected i.v. with *S. aureus* MW2 ($1 \times 10^7$ CFU). (B) Survival of the mice was recorded for 7 days after *S. aureus* MW2 infection. The percentage of surviving mice in each treatment group is shown (n=10/group). (C) Two days after *S. aureus* MW2 infection, the mice were sacrificed, indicated tissues removed, and homogenized in PBS solution. The solution were diluted, and plated on the agar plates to measure colony forming unit (CFU) of *S. aureus* MW2 (n=5/group). (D) Histopathology of the indicated tissues on two days after infection. Scale bar, 10 μm. 1826, CpG-DNA 1826; MW2, *S. aureus* MW2. These results are expressed as representatives of three independent experiments.

FIG. 2. Changes of cell populations in mouse peritoneal cavity, spleen, and bone marrow after *S. aureus* MW2 infection. BALB/c mice were administered i.p. with CpG-DNA 1826. After 7 days, the mice were injected i.v. with *S. aureus* MW2 ($1 \times 10^7$ CFU). On 2 days after *S. aureus* MW2 infection, the mice were sacrificed. The peritoneal cavity cells, splenocytes, and bone marrow cells were harvested and stained with fluorescence-conjugated antibodies to analyze the cell populations through flow cytometry. (A) Peritoneal cavity cells. (B) Bone marrow cells. (C) Splenocytes. n=3/group. 1826, CpG-DNA 1826. MW2, *S. aureus* MW2. These results are expressed as representatives of three independent experiments.

FIG. 3. Production of antibodies in mouse peritoneal cavity by CpG-DNA 1826 administration. Mice were administrated i.p. with CpG-DNA 1826 or non-CpG-DNA 2041 for indicated periods. On 1, 3, and 7 days after the administration, supernatant of peritoneal cavity (A) and sera (B) were harvested to measure the levels of total IgG by means of ELISA (n=3/group). These results are expressed as representatives of three experiments.

FIG. 4. Production of bacteria-reactive antibodies in mouse peritoneal cavity and serum by administration of CpG-DNA 1826. (A, B) BALB/c mice were administered i.p. with CpG-DNA 1826. After 7 days, the mice were injected i.v. with *S. aureus* MW2 ($1 \times 10^7$ CFU). 2 days after the bacteria infection, supernatants of peritoneal cavity and sera were collected from the mice. Bacteria-reactive antibodies in the peritoneal cavity (A) and sera (B) were captured using *S. aureus* MW2 coated plates (n=3/group) and the amounts of total IgG and each IgG isotype were measured by ELISA. 1826, CpG-DNA 1826. MW2, *S. aureus* MW2. (C-F) BALB/c (C, D) and TLR9 −/− (E, F) mice were administrated i.p. with CpG-DNA 1826. On 7 days after administration of CpG-DNA 1826, supernatants of peritoneal cavity (C, E) and sera (D, F) were collected. To measure the amounts of antibodies reactive to Gram-positive bacteria, indicated bacteria were coated on the poly-L-lysine coated plates. Amounts of total IgG were determined by means of ELISA (n=3/group). These results are expressed as representatives of three independent experiments.

FIG. 5. Production of bacteria-reactive antibodies in mouse peritoneal cavity cells by treatment with CpG-DNA 1826 in vitro. BALB/c mice were administered i.p. with PBS, CpG-DNA 1826 or non-CpG-DNA for 7 days. (A) Cells of peritoneal cavity were harvested and then stimulated with PBS, CpG-DNA 1826 or non-CpG-DNA 2041. After 48 h, the cell culture supernatants were collected and then amounts of total IgG were determined by means of ELISA (n=3/group). (B) The peritoneal cavity cells from PBS-injected mice were stimulated with PBS, CpG-DNA 1826 or non-CpG-DNA 2041. To measure the amounts of antibodies reactive to Gram-positive bacteria, indicated bacteria were coated on poly-L-lysine coated plates and the cell culture supernatants were applied. Amounts of bound IgG were determined by means of ELISA (n=3/group). (C) After administration of BALB/c i.p. with PBS or CpG-DNA 1826, B1 and B2 cells of peritoneal cavity were isolated by FACSAria™ II using fluorescence-labeled anti-mouse CD19 and anti-mouse CD23 antibodies. (D and E) Isolated B1 cells and B2 cells from peritoneal cavity were stimulated with PBS or CpG-DNA 1826. After 48 h, the cell culture supernatants were collected. The amounts of total IgG (D) and the amounts of antibodies reactive to Gram-positive bacteria (E) were determined by means of ELISA (n=3/group). 1826, CpG-DNA 1826; 2041, non-CpG-DNA 2041. These results are expressed as representatives of three experiments.

FIG. 6 Enhancement of phagocytosis by CpG-DNA 1826-induced polyclonal antibodies in mouse macrophage cell lines. (A and B) BALB/c mice were administered i.p. by PBS (A) or CpG-DNA 1826 (B). After 7 days, the supernatants of peritoneal cavity were collected and polyclonal antibodies were purified with Protein A affinity bead. The purified antibodies were prepared with reducing (R) or non-reducing (NR) sample buffer, and subjected to SDS-PAGE and staining with Coomassie brilliant blue R-250 solution. (C) Binding ability of the antibodies (10 μg/ml) with $S.$ $aureus$ MW2 was measured by ELISA. PC Ab, purified antibodies from PBS-administered peritoneal cavity. 1826 PC Ab, purified antibodies from CpG-DNA 1826-administered peritoneal cavity. The absorbance was read at 450 nm. (D) FITC-labeled $S.$ $aureus$ MW2 ($3 \times 10^8$ CFU/ml) were incubated with PBS, PC Ab or 1826 PC Ab (10 μg/ml) for 1 h, and treated to the RAW 264.7 cells. After 1 h, the RAW 264.7 cells were washed with PBS, fixed, and then stained with Hoechst No. 33258 to visualize the nuclei (blue). Confocal images showed phagocytosis of $S.$ $aureus$ MW2. Scale bars, 10 μm. (E) Phagocytosis index was analyzed. (n=3/group). Phagocytosis index means the number of FITC-labeled $S.$ $aureus$ MW2 taken by the macrophage. These results are expressed as representatives of three experiments.

FIG. 7. Screening of hybridoma clone in HAT and HT medium producing bacteria-reactive monoclonal antibody. (A) ELISA results from the initial screening of a cell-fusion experiment in HAT media. The peritoneal cells of the CpG-DNA 1826-administered mice were harvested, and fused with mouse SP2/0 myeloma cells. Bacteria-reactive antibody-producing hybridoma clone was screened by HAT medium using $S.$ $aureus$ MW2 coated plates. (B) ELISA results of the 6 clones from FIG. 7A using $S.$ $aureus$ MW2 coated plates. (C) ELISA results of the 4 clones from FIG. 7B using $S.$ $aureus$ MW2 coated plates. (D) 3F5 hybridoma clone from FIG. 7A was selected for the production of monoclonal antibody following subcloning by limiting dilution method in HT media. (E) Hybridoma clones culture supernatants for the bacteria binding was analyzed using ELISA.

FIG. 8. The cDNA sequences for variable domains of heavy and light chains isolated from the hybridoma cell clone 3F5H6. (A) Sequence of the heavy chain variable domain. (B) Sequence of the light chain variable domain. Predicted amino acid sequences are indicated under the cDNA sequences.

FIG. 9 Enhancement of phagocytosis by monoclonal antibody produced from CpG-DNA 1826-stimulated mouse peritoneal cavity B cells. (A) Production of bacteria-reactive monoclonal antibody. Hybridoma cells (3F5H6 clone) producing bacteria-reactive monoclonal antibodies were obtained from B cells in CpG-DNA 1826-administered mouse peritoneal cavity by standard hybridoma technique. The ascites of mice induced by 3F5H6 clone was isolated, and the monoclonal antibody was purified with Protein A affinity column chromatography, subjected to SDS-PAGE, and stained with Coomassie brilliant blue R-250 solution. R, reducing; NR, non-reducing. (B) The isotype of the monoclonal antibody was determined by ELISA using $S.$ $aureus$ MW2-coated plates. (C) Bacteria-reactivity of the antibody was assessed by ELISA using indicated Gram-positive bacteria-coated plates (n=3/group). (D-G) FITC-labeled $S.$ $aureus$ MW2 cells ($3 \times 10^8$ CFU/mL) were incubated with PBS, normal mouse IgG or m3F5H6 monoclonal antibody (10 μg/mL) for 1 h, and treated to the RAW 264.7 cells (D and E) and peritoneal cavity cells (F and G) in vitro. After 1 h, the cells were washed with PBS, fixed, and then stained with Hoechst No. 33258 to visualize the nuclei (blue). (D and F) Confocal images showed phagocytosis of $S.$ $aureus$ MW2. Scale bars, 10 μm. RAW, RAW 264.7 cells; PC, peritoneal cavity cells. (E and G) Phagocytosis index was analyzed (n=3/group). (H) Enhancement of phagocytosis by the bacteria-reactive monoclonal antibody. FITC-labeled $S.$ $aureus$ MW2 cells ($3 \times 108$ CFU/mL) were incubated with normal mouse IgG or m3F5H6 monoclonal antibody (10 μg/mL) for 1 h and injected i.p. to BALB/c mice. After 1 h, peritoneal cells were harvested from the mice, and stained with specific cell markers for macrophages, dendritic cells, and neutrophils. The levels of phagocytosis were analyzed by flow cytometry (n=3/group). These results are expressed as representatives of three experiments.

FIG. 10 is a picture showing reactivity characteristics against bacteria of a monoclonal antibody (m3F5H6 monoclonal antibody) produced from CpG-DNA 1826-stimulated mouse peritoneal B cells. (A) Bacterial-reactive monoclonal antibody (m3F5H6) or normal mouse IgG (Nor mIgG) was captured using a plate coated with Gram(−) bacteria ($E.$ $coli$ K1, $A.$ $baumannii$, $P$ $aeruginosa$, $K.$ $pneumoniae$ 11418, $K.$ $pneumoniae$ 40145, $K.$ $pneumoniae$ 41293)) (n=3/group) and the titration curve was measured by ELISA. (B) Bacterial-reactive monoclonal antibody (m3F5H6) or normal mouse IgG (Nor mIgG) was captured using a plate coated with endocytic bacteria ($L.$ $monocytogenes$, $S.$ $typhimurium$) (n=3/group) and the titration curve was measured by ELISA.

FIG. 11. Effects of bacteria-reactive monoclonal antibody on survival of the $S.$ $aureus$ MW2-infected mice. (A) Schematic diagram of the experimental process. (B) Eight-week-old female BALB/c mice were injected i.v. with $S.$ $aureus$ MW2 ($1.5 \times 107$ CFU), and subsequently injected i.v. with PBS, normal mouse IgG or m3F5H6 IgG (25 mg/Kg mouse), and then survival rates were monitored for 7 days (n=10/group). (C) Two days after *S. aureus* MW2 infection, CFU of *S. aureus* MW2 in the indicated tissues was determined (n=5/group). (D) Histopathology of the indicated tissues on 2 days (D2) after infection. (E) Histopathology of the indicated tissues on 30 days (D30) after infection. Scale bar, 10 μm. MW2, *S. aureus* MW2. These results are expressed as representatives of three experiments.

FIG. 12 is a sequence analysis for constructing a humanized antibody, and the amino acid sequence of m3F5H6, a wild-type mouse-derived antibody of the present invention, a Samalizumab antibody having a human VH1-Vk1 subtype skeleton used for constructing a humanized antibody, and a humanized antibody h3F5H6 is divided into a variable heavy chain and a variable light chain and aligned in a straight line. Square brackets ([ ]) indicate each CDR region, the underline indicates an amino acid corresponding to the Bernie region, and an asterisk (*) indicates a reverse-substituted portion with an amino acid derived from a mouse m3F5H6 wild type antibody to maintain affinity. Triangles (▲) indicates a portion in which an amino acid that does not correspond to the Bernie region is reversely substituted with an amino acid derived from a mouse m3F5H6 wild type antibody in order to maintain affinity. At this time, the CDR region was defined according to Kabat numbering.

FIG. 13. Purification humanized bacteria-reactive antibody (h3F5H6). Humanized bacteria-reactive antibody (h3F5H6 IgG) antibody was purified using Protein-A agarose column chromatography and identified by SDS-PAGE and Coomassie blue staining.

FIG. 14. Characterization of humanized bacteria-reactive antibody (h3F5H6) recognizing bacteria. (A) Humanized bacteria-reactive antibody (h3F5H6 IgG) or normal human IgG was captured using Gram(+) bacteria (*S. aureus, S. aureus* MW2, *S. epidermidis, S. pyogenes*) coated plates (n=3/group) and the titration curves were measured by ELISA. (B) Humanized bacteria-reactive antibody (h3F5H6 IgG) or normal human IgG (normal hIgG) was captured using Gram(−) bacteria (*A. baumannii, E. coli* K1, *P. aeruginosa, K. pneumoniae* 11418, *K. pneumoniae* 40145, *K. pneumoniae* 41293) coated plates (n=3/group) and the titration curves were measured by ELISA.

FIG. 15 is a diagram showing the characteristics of a humanized bacterium-reactive antibody (h3F5H6) that recognizes bacteria. Humanized bacterial-reactive antibody (h3F5H6 IgG) or normal human IgG was captured using a plate coated with intracellular parasitic bacteria (*L. monocytogenes, S. typhimurium*) (n=3/group) and the titration curve was measured by ELISA.

FIG. 16. Effects of humanized bacteria-reactive antibody (h3F5H6) on survival of the *S. aureus* MW2-infected mice. (A) Schematic diagram of the experimental process. (B) Eight-week-old female BALB/c mice were injected i.v. with *S. aureus* MW2 (1.5×10$^7$ CFU), and subsequently injected i.v. with PBS, normal human IgG (normal hIgG) or h3F5H6 IgG (25 mg/Kg mouse), and then survival rates were monitored for 7 days (n=10/group). (C) Histopathology of the indicated tissues on 2 days (D2) after infection. Scale bar, 10 μm. MW2, *S. aureus* MW2.

FIG. 17 shows the effect for the survival rate of mice against *S. aureus* MW2-infection of the humanized bacterial-reactive antibody (h3F5H6) that cobra venom factor (CVF) was administered to the peritoneal cavity of mice to remove complement and humanized in these mice. (A) Schematic diagram of the experimental process. (B) CVF (30 μg/mouse) was administered to 8-week-old female BALB/c mice i.p. and after 6 hours *S. aureus* MW2 (1×10$^7$ CFU) was injected i.v., PBS or h3F5H6 IgG (25 mg/Kg mouse) was injected with i.v., and the survival rate was monitored for 7 days (n=10/group).

FIG. 18 is a diagram showing that CpG-DNA protects mice from *E. coli* K1 infection. (A) Schematic diagram of the experimental process. BALB/c mice were administered CpG-DNA 1826 by i.p. After 7 days, mice were injected with *E. coli* K1 (1×10$^6$ CFU) with i.p. (B) The survival of mice was recorded for 2 days of *E. coli* K1 infection. The percentage of surviving mice in each treatment group was shown (n=12/group). (C) One day after *E. coli* K1 infection, the mouse was sacrificed, the indicated tissue was removed, and homogenized in PBS solution. The solution was diluted and plated on an agar plate to measure the CFU (colony forming unit) of *E. coli* K1 (n=5/group). (D) Histopathology of indicated tissues 1 day after infection. Scale bar, 10 μm. 1826, CpG-DNA 1826.

FIG. 19 is a diagram showing that CpG-DNA protects mice from which complement has been removed from *E. coli* K1 infection. (A) Schematic diagram of the experimental process confirming that CVF removes complement. (B) BALB/c mice were administered CpG-DNA 1826 by i.p. After 7 days, mice were administered with CVF (30 μg/mouse) i.p., and the amount of complement (C3) in the serum was measured by ELISA. (C) Schematic diagram of the experimental procedure in which CpG-DNA protects mice from *E. coli* K1 infection in mice which complement has been removed. (D) BALB/c mice were administered CpG-DNA 1826 by i.p. After 7 days, mice were administered with CVF (30 μg/mouse) i.p., and 6 hours later, mice were injected with *E. coli* K1 (3×10$^5$ CFU) i.p. (n=12/group). The survival of mice was recorded for 2 days of *E. coli* K1 infection.

FIG. 20. Effects of humanized bacteria-reactive antibody (h3F5H6) on survival of the *E. coli* K1-infected mice. Eight-week-old female BALB/c mice were injected i.p. with *E. coli* K1 (5×10$^6$ CFU), and subsequently injected i.v. with PBS, normal human IgG (normal hIgG) or h3F5H6 IgG (25 mg/Kg mouse), and then survival rates were monitored for 18 hours (n=10/group).

MODE FOR INVENTION

Hereinafter, the embodiments of the present invention will be described in detail with reference to the attached exemplary drawings, as such an example, a person skilled in the art to which the present invention pertains may be implemented in various different forms, it is not limited to the embodiment described here.

Example 1: Mice

Eight-week-old BABL/c mice were purchased from Nara Biotech, Inc. (Seoul, Korea) and BALB/c TLR9 knockout mice were purchased from Oriental Bioservice, Inc. (Kyoto, Japan). The mice were maintained in specific-pathogen-free (SPF) condition with suitable temperature (20~25° C.) and humidity (32~37%). The mice were sacrificed under isoflurane (JW Pharmaceutical, Seoul, Korea) anesthesia to minimize pain. All protocols of animal studies were approved by the Institutional Animal Care and Use Committee of Hallym University (Permit Number: Hallym 2014-66, 2015-54, 2016-22, 2016-36).

Example 2: CpG-DNA

CpG-DNA 1826 and non-CpG-DNA 2041 were purchased from GenoTech (Daejeon, Korea). Backbones of these sequences were modified with phosphorothioate. The following sequences of oligodeoxynucleotides were used: CpG-DNA 1826, 5'-TCCATGACGTTCCTGACGTT-3' (SEQ. ID No. 9), non-CpG-DNA 2041, 5'-CTGGTCTTTCTGGTTTTTTTCTGG-3' (SEQ. ID No. 10). The non-CpG-DNA 2041 was usually used as a negative control. CpG-DNA 1826 was dissolved in distilled water, and 50 μg of CpG-DNA 1826 was injected intraperitoneally (i.p.) to mice for the indicated time periods.

Example 3: Bacteria Culture and Infection Studies In Vivo

S. aureus (KCCM 12103), Staphylococcus epidermidis (S. epidermidis, KCCM 40416), Streptococcus pyogenes (S. pyogenes, KCCM 11873), A. baumannii (KCCM 40203), E. coli K1 (KCCM 12119), Pseudomonas aeruginosa (P. aeruginosa, KCCM 11803), K. pneumoniae 11418 (KCCM 11418), K. pneumoniae 40145 (KCCM 40145), K. pneumoniae 41293 (KCCM 41293) were purchased from Korean Culture Center of Microorganisms (KCCM, Seoul, Korea). S. aureus, strains MW2 (MRSA) was obtained from Professor Bok Luel Lee (Pusan National University). All bacteria except S. aureus MW2 were grown at 37° C. in Lysogeny broth (LB). S. aureus MW2 was grown at 37° C. in Columbia broth supplemented with 2% NaCl. All bacteria were grown overnight and re-cultured in a fresh media with 1/50 dilution until OD600 0.5~0.6, the mid log phase, and harvested. The S. aureus MW2 was washed with PBS, centrifuged, and suspended at 5×10$^7$ colony forming units (CFU)/mL in PBS. 0.2 mL of the bacterial suspension was injected intravenously (i.v.) to mice. The infected mice were observed for morbidity or recovery for 7 days. We investigated the survival rate, histopathology, bacterial loads (CFU) in tissues, cell population of tissues, and measured quantity of antibody in peritoneal cavity and serum in infected mice.

Example 4: H&E Staining

Paraffin embedding and sectioning of each tissue was processed by conventional methods (Kwon, S., D. Kim, B. K. Park, S. Cho, K. D. Kim, Y. E. Kim, C. S. Park, H. J. Ahn, J. N. Seo, K. C. Choi, D. S. Kim, Y. Lee, and H. J. Kwon. 2012. PLoS One 7: e33121; Weiss, A. T., N. M. Delcour, A. Meyer, and R. Klopfleisch. 2011. Vet Pathol 48: 834-838). After infection with S. aureus MW2 in mice, tissues including liver, lung, kidney, spleen were prepared and mounted on the slides, and dried at 40° C. overnight. Then, the tissue slides were incubated at 60° C. to melt paraffin for 30 min. The tissues were incubated in xylene, rehydrated through a series of 100~70% ethanol, and washed with distilled water. The tissues were stained with Gill's Hematoxylin V (Muto Pure Chemicals, Tokyo, Japan), washed with water, and secondly stained with Eosin Y solution (Sigma-Aldrich, St. Louis, MO, USA). Stained tissues were dehydrated in 70~100% ethanol, incubated in xylene, and mounted with Malinol (Muto Pure Chemicals). Stained tissues were observed with Eclipse E200 microscope (Nikon, Japan).

Example 5: Analysis of Colony Forming Units

On 2 days after infection, each tissue was harvested, weighed, and homogenized with PBS in 2 mL tube (Eppendorf, Hamburg, Germany) with stainless steel beads (Qiagen, Hilden, Germany). The mixed solution was transferred to 6 well plates containing Columbia broth-Bacto agar, and then colonies were counted after overnight incubation at 37° C.

Example 6: Preparation of Serum, Peritoneal Cells, Splenocytes, and Cells of Bone Marrow After two days of infection with S. aureus MW2 in mice, the mice were anesthetized with isoflurane. Sera were prepared from mice by a heart-punching method. Peritoneal cells, splenocytes, and cells of bone marrow were harvested with RPMI 1640 medium containing 5% fetal bovine serum (FBS) from the mice as described previously (Fortier, A. H., and L. A. Falk. 2001. Curr Protoc Immunol Chapter 14: Unit 14 11; Pineda-Torra, I., M. Gage, A. de Juan, and O. M. Pello. 2015. Methods Mol Biol 1339: 101-109; Ray, A., and B. N. Dittel. 2010. J Vis Exp.; Stagg, A. J., F. Burke, S. Hill, and S. C. Knight. 2001. Methods Mol Med 64: 9-22). After the cells were collected, erythrocytes were removed by red blood cell lysis buffer (140 mM NH4Cl, 20 mM Tris-HCl (pH7.2)). The prepared cells were suspended with RPMI 1640 medium containing 5% FBS for stimulation with CpG-DNA in vitro, and dispensed to 96 well tissue culture plates (BD Falcon, Falcon, Mexico).

Example 7: Flow Cytometry

The cells prepared from mice were blocked with anti-mouse CD16/32 (BD Biosciences, San Jose, CA, USA) for 10 min and stained with following fluorescence-labeled antibodies: anti-mouse CD8, CD11c, CD3, CD4, CD11b, CD19 (BD Biosciences, USA), CD23, F4/80, Ly-6G antibodies (eBioscience, San Diego, CA USA). The samples were washed with PBS containing 1% FBS, and analyzed by FACSCanto™ II (Becton Dickinson, Franklin Lakes, NJ, USA).

Example 8: ELISA

To determine bacteria-specific antibody production by CpG-DNA 1826 administration and/or S. aureus MW2 infection in mice, we used poly-L-lysine coated plate (Corning Inc, Corning city, NY, USA). Overnight-grown bacteria were washed with PBS two times by centrifugation at 10,000 rpm for 15 min, and re-suspended with conventional ELISA coating buffer. Each well was coated with 100 μL of re-suspended bacteria overnight at 4° C. After incubation, the bacteria were fixed with 0.5% glutaraldehyde in PBS for 15 min at room temperature. After washing twice with PBS, each well was incubated with RPMI 1640 solution containing 100 mM glycine and 0.1% BSA for 30 min at room temperature to block glutaraldehyde and washed twice with PBS. The bacteria-coated wells were blocked with PBS containing 1% BSA for 1 h at room temperature. Serum, supernatants of peritoneal cavity and peritoneal cell culture or purified antibodies were added to each well with serial dilution, and incubated for 1 h at room temperature. The samples were washed 3 times with PBS-T (0.2% Tween-20 in PBS) and antibodies including horse radish peroxidase (HRP)-labeled goat anti-mouse IgG (BD Biosciences, San Jose, CA, USA), IgG1, IgG2a, IgG2b, or IgG3 (Southern Biotech, Birmingham, AL, USA) were added to the wells for 1 h at room temperature. After washing with PBS-T four times, TMB Microwell Peroxidase Substrate Kit (KPL, Gaithersburg, MD, USA) was used to develop blue-color expression, and fixed with TMB Stop solution (KPL) to sustain yellow-color, and measured absorbance at the 450 nm using Spectra Max 250 microplate reader (Molecular Devices, Sunnyvale, CA, USA). To determine the amounts of antibodies by ELISA, goat anti-mouse IgG (BD Biosciences) was coated overnight at 4° C. The wells were blocked with PBS containing 1% BSA for 1 h at room temperature, and amounts of total IgG and IgG isotypes were measured by ELISA as previously described (Kwon, S., D. Kim, B. K. Park, S. Cho, K. D. Kim, Y. E. Kim, C. S. Park, H. J. Ahn, J. N. Seo, K. C. Choi, D. S. Kim, Y. Lee, and H. J. Kwon. 2012. PLoS One 7: e33121).

Example 9: Stimulation of Mouse Peritoneal Cells with CpG-DNA In Vitro

Peritoneal cells were harvested from mice with RPMI 1640 medium containing 5% FBS. After removal of erythrocytes, the cells were washed with RPMI 1640 medium containing 5% FBS, and cultured with RPMI 1640 medium containing 5% FBS with 100 U/mL of penicillin and 100 µg/mL of streptomycin. 5 µg/mL of CpG-DNA 1826 was treated to each cell culture plate. After 48 h, cell culture supernatants were harvested and analyzed with ELISA to quantify the antibodies.

Example 10: Sorting of B Cells from Mouse Peritoneal Cells

Anti-mouse CD19 (BD Bioscience) was stained for designation of B cells, and anti-mouse CD23 (eBioscience) was stained for separated sorting of B1 and B2 cells. Anti-mouse CD3 (BD Bioscience) was used for staining of T cells to separate non-B cells from lymphocytes. Peritoneal cells were stained with antibodies, washed, and suspended with sorting buffer (1 mM EDTA, 25 mM HEPES pH7.0, 1% FBS diluted in PBS). B1 cells and B2 cells were sorted by FACSAria™ II (Becton Dickinson).

Example 11: Purification of Polyclonal Antibodies from Mouse Peritoneal Cavity The mice were i.p. administered with PBS or CpG-DNA 1826. On 7 days after administration, supernatants of peritoneal cavity were obtained by centrifugation to remove peritoneal cells. Polyclonal antibodies in the cell-removed supernatants of peritoneal cavity were purified using Protein A affinity chromatography (Repligen, Waltham, MA, USA) and analyzed by SDS-PAGE. Binding ability of these antibodies against *S. aureus* MW2 was measured by ELISA as described above.

Example 12: Production of Hybridoma Cells from B Cells of Peritoneal Cavity to Obtain Bacteria-Reactive Monoclonal Antibody To obtain hybridoma cells producing bacteria-reactive antibody, BALB/c mice were injected i.p. with 50 µg of CpG-DNA 1826. The peritoneal cells of the mice were harvested after 7 days, fused with mouse SP2/0 myeloma cells, and bacteria-reactive antibody-producing hybridoma clone (m3F5H6) was screened by standard hybridoma technique (Kim, D., S. Kwon, J. W. Rhee, K. D. Kim, Y. E. Kim, C. S. Park, M. J. Choi, J. G. Suh, D. S. Kim, Y. Lee, and H. J. Kwon. 2011. BMC Immunol 12: 29; Yokoyama, W. M., M. Christensen, G. D. Santos, and D. Miller. 2006. Curr Protoc Immunol Chapter 2: Unit 2 5). To obtain ascites, BALB/c mice were injected i.p. with the hybridoma clone after pristine injection. After 9~11 days, ascites were harvested from the mouse peritoneal cavity. The monoclonal antibody was purified from the ascites using Protein An affinity chromatography (Repligen) and analyzed by SDS-PAGE. Isotype and the bacteria-reactivity of the monoclonal antibody was measured by ELISA as described above.

Example 13: Cloning of Variable Heavy Chain and Light Chain (Fab) of Bacterial-Reactive Monoclonal Antibody Hybridoma cells producing bacterial-reactive monoclonal antibody (m3F5H6) were cultured, total RNA was extracted from the hybridoma cells, and cDNA was synthesized by reverse transcription. In order to clone the Fab sequence of the bacteria-reactive monoclonal antibody, the generated cDNA was amplified using AccuPrime Taq DNA polymerase (Invitrogen) and the following primers. Heavy chain primers, IGG2b: GGAAGATCTAGGGGCCAGTGGATA-GACTGATGG (SEQ ID NO: 11), 5'MH2: CTTCCGGAAT-TCSARGTNMAGCTGSAGSAGTCWGG (SEQ ID NO: 12); Kappa chain primers, 3'Kc: GGTGCATGCGGATA-CAGTTGGTGCAGCATC (SEQ ID NO: 13), 5'Mk: GGGAGCTCGAYATTGTGMTSACMCARWCTMCA (SEQ ID NO: 14).

Standard PCR reaction was carried out 25 cycles. The PCR product was directly ligated into pGEM-T easy vector (Promega). The cloned mouse Ig insert was analyzed by DNA sequencing.

Example 14: Sequence Analysis of Variable Fragments (Fv) and Molecular Modeling The immunoglobulin variable domain sequence of m3F5H6 was analyzed by IgBLAST (http://www.ncbi.nlm.nih.gov/igblast/) (Ye J, Ma N, Madden T L, Ostell J M. IgBLAST: Nucleic Acids Res. 2013; 41(Web Server issue): W34-4027). Six CDRs (complementarity determining regions) were determined by Kabat numbering (Kabat E A, Wu T T. J Immunol. 1991; 147(5):1709-1719), and some framework (FR) residues of m3F5H6 mAb were grafted with human VH1-Vk1 subfamily and in this case, the three-dimensional structure of the Samalizumab framework, mouse and humanized 3F5H6 Fv amino acid sequence was simulated using a web modeling program, ROSIE (Lyskov S, Chou F C, Conchuir S O, Der B S, Drew K, Kuroda D, Xu J, Weitzner B D, Renfrew P D, Sripakdeevong P, Borgo B, Havranek J J, Kuhlman B, et al. PLoS One. 2013; 8(5):e63906). This program identifies most homologous templates for the FRs and CDRs of the heavy and light chains and combines this template structure into an optimized model.

Example 15: Construction of 3F5H6 Humanized Antibody

Determination of CDRs of Non-Human (Mouse)-Derived Antibodies

For humanization, it is first necessary to determine the CDRs of the antibody. Methods for determining CDRs include Kabat numbering based on the diversity of amino acid sequences, Chothia numbering based on the structure of the loop region (Dunbar J, Krawczyk K, Leem J, Baker T, Fuchs A, Georges G, Shi J, Deane C M. Nucleic Acids Res. 2014; 42:D1140-1146), and IMGT numbering (Lefranc M P. Nucleic Acids Res. 2001; 29(1):207-209) based on high preservation of variable region structures, Kabat numbering is the most widely used. The CDRs of the bacterial-reactive mouse-derived antibody were determined according to Kabat numbering (see FIG. 8).

Selection of Human Antibody Skeleton Suitable for Humanized Antibody Construction and Grafting of Wild-Type Antibody CDR Regions The variable regions of human antibodies are largely divided into 7 subtypes (VH1,VH2,VH3,VH4,VH5,VH6, VH7) for heavy chains and 17 subtypes for light chains (κ1, κ κ κ κ κλλλλλλλλλλλλλλλλλλλ), since amino acid sequences of each subtype are different, the biophysical structure and the stability is different accordingly, and accordingly, the frequency used in the natural human antibody repertoire is also different (Tiller T, Schuster I, Deppe D, Siegers K, Strohner R, Herrmann T, Berenquer M., Poujol D, Stehle J, Stark Y, et al. MAbs, 2013; 5(3):445-470).

In general, when humanized antibodies are produced using the CDR grafting method, in order to maintain the structure of the CDR as much as possible, it is transferred to a human skeleton that has very high sequence homology with a wild-type non-human antibody and in this case, the subtype of the humanized antibody transferred is naturally stable. However, in the case of a subtype with a low frequency, there is a possibility that an antibody with low stability can be obtained after humanization.

In order to determine a human skeleton suitable for humanization of antibodies derived from bacteria-reactive mice, Through Igblast (URL: http://www.ncbi.nlm.nih.gov/igblast/), the subtype of the human antibody variable region having the highest sequence homology with the existing wild-type antibody was searched, and as a result, it was confirmed that the homology was highest with the VH1 and Vk1 subtype of the human antibody. Therefore, in the present invention, in order to construct a humanized antibody with high stability while maintaining the affinity for the antigen and its function, an antigen-binding site was grafted into VH1-Vk1 subtype skeleton of the human antibody. The VH1-Vk1 subtype used the skeleton of a therapeutic antibody (Samalizumab) (Kretz-Rommel A, Qin F, Dakappaqari N, Cofiell R, Faas S J, Bowdish K S. J Immunol 2008; 180:699-705). For the constant regions of the heavy and light chains of the humanized antibody, the backbone of a commercially available therapeutic antibody (Herpceptin) was used. The thermodynamic stability and expression yield of Herceptin has been sufficiently demonstrated by the results of previous studies, and has been particularly successfully used for humanization of various mouse antibodies (Carter P, Presta L, Gorman C M, Ridgway J B, Henner D, Wong W L, Rowland A M, Kotts C Carver M E, Shepard H M. Proc Natl Acad Sci USA 1992; 89(10):4285-4289; Presta L G, Chen H, O'Connor S J, Chisholm V, Meng Y G, Krummen L, Winkler M, Ferrara N. Cancer Res. 1997; 57(20):4593-4599).

Selection of Additional Conserved Amino Acids for Grafting of Wild-Type Mouse Antibody CDR Regions and Maintaining Affinity As mentioned above, since the humanized antibody constructed by a simple CDR grafting method often decreases its function when compared to a wild-type non-human antibody, the amino acid located in the Bernier region, and located in the antibody skeleton at the same time as the CDR grafting was proceeded with additionally reversely substituted clone (h3F5H6). There are a total of 30 amino acids located in the Bernie region in the variable region, 16 in the variable heavy chain region, and 14 in the variable light chain region. Through sequence analysis between the wild-type mouse antibody and the selected VH1-Vk1 human antibody framework subtype, it is confirmed that six amino acids (68,70,72,74,97,98) in the variable heavy chain region and four (36,49,69,71) amino acids in variable light chain region among the amino acids in the total 30 Bernie region, was different (see FIG. 11). In particular, 4 amino acids (26-30th amino acid residues) in the variable heavy chain region play an important role in maintaining the canonical structure through the interaction between CDR1 and CDR2 in the literature (Foote J, Winter G. J Mol Biol. 1992; 224(2)).:487-499). Therefore, since it is expected to stabilize the structure of the CDR of the grafted wild-type antibody, it is preferable to use the sequence of the existing mouse antibody Amino acid 71 in the heavy chain variable region also plays an important role in determining the arrangement of CDR1 and 2, the characteristics of the CDR depend on whether an amino acid with a bulky residue (lysine or arginine) or an amino acid with a small residue (valine, alanine) comes at this position. The wild-type mouse antibody has lysine at position 74 in the heavy chain, which has the opposite property to glutamine at position 74 in the human VH1 subtype skeleton, so it was reverse substituted, and in addition, amino acids 68, 70, and 72 in the human VH1 subtype heavy chain variable region were inversely substituted with the amino acid sequence of the wild-type mouse antibody.

The base and amino acid sequences of the human VH1-Vk1 subtype for sequence analysis were those of Samalizumab, an antibody having the skeleton of the above subtype.

In addition to the Bernie region, the VH/VL interface amino acids that affect stability are regions that affect the stability of the entire antibody by stabilizing the binding of the variable heavy and light chain regions as their residues face the interior rather than the surface of the antibody. Most antibodies are made up of the same amino acid residues.

First, the variable region sequences of candidate clones and wild-type mouse antibodies obtained primarily through amino acid sequence analysis were entered into antibody modeling part in an online server (URL: http://rosie.rosettacommons.org/; Lyskov S, Chou F C, Conchuir S O, Der B S, Drew K, Kuroda D, Xu J, Weitzner B D, Renfrew P D, Sripakdeevong P, Borgo B, Havranek J J, Kuhlman B, et al. PLoS One. 2013; 8(5):e63906) respectively and the predicted structure was obtained. Each of the obtained structures overlapped the structure of the protein to observe the structural change of the CDR loop. It was confirmed that the six CDRs grafted on the overlapping structure have a structure that does not deviate significantly when compared to the CDRs of a wild-type mouse antibody, and in particular, the orientation of amino acid residues in the CDR loop that can affect antigen binding is mostly consistent with wild-type mouse antibody.

Example 16: Construction and Expression of Humanized Bacterial-Reactive Antibodies In order to obtain a humanized IgG1 Ab having an Intact IgG format, VH and Vk coding genes were synthesized including restriction enzyme sites at both 5' and 3' ends (Bioneer, Korea). These genes were inserted into a modified pcDNA 3.4 expression vector (Invitrogen) carrying a human IgG1 fixation site (CH1-hinge-CH2-CH3) or a human kappa chain fixation site (CL) for mammalian cell expression in HEK 293F cells. Humanized bacterial-reactive antibodies were produced using the HEK 293F expression system and after 5-7 days incubation were purified using Protein A affinity chromatography according to the manufacturer's protocol. Mouse parent and humanized antibodies were evaluated for their purity by SDS-PAGE analysis.

Example 17: Construction of Humanized Antibody Gene in IgG Form

The nucleotide sequence of the designed humanized antibody basically follows the nucleotide sequence of the commercialized high-yield therapeutic antibody Samalizumab, but with considering the codon frequency (Sequences of Proteins of Immunological Interest, US Dept. Health and Human Services)., 1991) other parts except the sequence were modified and design a base sequence encoding the amino acid sequence of the heavy chain variable region and the light chain variable region of a humanized antibody. The designed nucleotide sequence was synthesized by introducing a restriction enzyme recognition sequence for cloning into an animal cell expression vector at both ends of 5' and 3'(Bioneer, Korea).

The synthesized gene can be received in the state of being cloned into the pBHA vector, which is a basic vector provided by Bioneer. for expression in a complete IgG form, it was cloned using a restriction enzyme recognition sequence introduced during synthesis into an animal expression vector containing a heavy chain constant region and a light chain constant region, respectively. At this time, the amino acid and nucleotide sequences of the constant regions of the heavy and light chains follow the nucleotide sequence of the commercialized high yield therapeutic antibody, Herceptin.

Example 18: Expression and Purification of Antibodies

Expression of humanized bacterial-reactive antibody was performed by transient transfection of a mixture of light and heavy chain expression vectors and polyethyleneimine (Polyethylenimine, PEI) (Polyscience) into HEK293-F (Invitrogen) cells to culture in a shake flask containing serum-free FreeStyle 293 expression medium (Invitrogen). The detailed method is as follows.

Upon 200 mL transfection into a shake flask (Corning), HEK293-F cells were seeded in 100 ml of medium at a density of $2.0 \times 10^6$ cells/ml, and cultured at 150 rpm, 8% CO2. To produce each humanized antibody, the heavy and light chain plasmids were diluted in 10 ml FreeStyle 293 expression medium (Invitrogen) with 125 µg of heavy chain and 125 µg of light chain with a total of 250 µg (2.5 µg/ml), and was mixed with diluted 10 ml of medium diluted with 750 µg of PEI (7.5 µg/ml) and reacted at room temperature for 10 minutes.

Thereafter, the reacted mixed medium was put into the cells previously seeded at 100 ml and incubated at 150 rpm and 8% CO2 for 4 hours, and then the remaining 100 ml of FreeStyle 293 expression medium was added and incubated for 5 to 7 days. During cultivation, the protein produced by the cell, that is, the humanized antibody in the form of IgG, is secreted out of the cell by the cell and accumulated in the medium. Therefore, the humanized antibody was purified using a Protein A Sepharose column (GE healthcare) from the cell culture supernatant collected after cell culture by centrifugation at 2500 rpm for 20 minutes.

At this time, the purification method refers to the standard protocol provided by the Protein A column company, and the purified protein was measured for absorbance at a wavelength of 562 nm using a solution in the BCA protein assay kit (Thermo), and the amount was quantified according to the drawn standard curve. The size and purity of the purified antibody were analyzed by reducing SDS-PAGE. As shown in FIG. 12, it was confirmed that the bacterial-reactive humanized antibody of the present invention, h3F5H6 IgG, has a molecular weight of about 150 kDa and is purified to a purity of 99% or more.

Example 19: Fluorescent Labeling of Bacteria

S. aureus MW2 grown up to OD600 0.5~0.6 ($3 \times 10^8$ CFU) were harvested, washed, and fixed with 70% ethanol in PBS for 1 h. The fixed bacteria were labeled with 0.02 mM FITC (Sigma-Aldrich) in 0.1 M Na2CO3 buffer (pH 8.5) for 30 min at room temperature, washed with serum-free HBSS, and then re-suspended with HBSS containing 2 mM CaCl2, 1 mM MgCl2, 10 mM HEPES, 150 mM NaCl, and 0.4% BSA.

Example 20: Phagocytosis Assays In Vitro

The mouse macrophage cell line, RAW 264.7, was purchased from American Type Culture Collection (ATCC, Manassas, VA, USA). Cells were cultured in Dulbecco's Modified Eagle's Medium (DMEM) with 10% PBS, 100 U/mL of penicillin and 100 µg/mL of streptomycin. RAW 264.7 cells and mouse peritoneal cells were cultured on the poly-L-lysine (Sigma) coated-cover glass in 12 well plates (Nunc, Roskilde, Denmark) overnight. FITC-labeled S. aureus MW2 were incubated with PBS or antibodies for 1 h and then the bacteria were added to 12 well plates. After 1 h incubation, the cells were fixed with 4% paraformaldehyde (Affymetrix, Santa Clara, CA, USA), washed with PBS, and stained with Hoechst No. 33258 (Sigma-Aldrich) to identify cell nuclei at room temperature. The mounted cells were analyzed with a LSM 710 laser scanning microscope (Carl Zeiss, Oberkochen, Germany). Phagocytosis index was measured by counting the number of FITC-labeled S. aureus MW2 phagocytosed in RAW 264.7 cells and mouse peritoneal cells as described previously (Sun, R., L. Qiu, F. Yue, L. Wang, R. Liu, Z. Zhou, H. Zhang, and L. Song. 2013. Fish Shellfish Immunol 34: 38-45).

Example 21: Uptake of S. aureus MW2 in Mouse Peritoneal Cavity

To determine the influence of antibodies on phagocytosis in mouse peritoneal cavity, the mice were injected i.p. with the FITC-labeled S. aureus MW2. After 1 h, peritoneal cells were harvested, and stained with specific cell markers; anti-F4/80, CD11b, CD11c, and Gr-1 antibodies. Phagocytosis of macrophages, dendritic cells, and neutrophils in peritoneal cavity was measured by FACS analysis with FACSCanto™ II (Becton Dickinson).

Example 22: Analysis of Antibody Effect on S. aureus MW2 & E. coli K1 Infection In Vivo BABL/c mice were injected i.v. with $1.5 \times 10^7$ CFU of S. aureus MW2, and then i.v. injection of normal mouse IgG, monoclonal antibody (m3F5H6), normal human IgG, humanized antibody (h3F5H6) ((25 mg/kg mouse) were followed. Normal mouse IgG was purchased from Invitrogen (Carlsbad, CA, USA). BABL/c mice were also injected i.p. with 5×106 CFU of E. coli K1, and then i.v. injection of normal human IgG, humanized antibody (h3F5H6) ((25 mg/kg mouse) were followed. After injection of antibodies, survival rate over 7 days (for S. aureus MW2) or 18 h (for E. coli K1) was monitored. Two days after S. aureus MW2 or infection, the mice were sacrificed, indicated tissues removed, and then CFU and histopathology of S. aureus MW2 was monitored.

Example 23: Analysis of the Effect of Antibodies in Mice from which Complement was Removed Against S. aureus MW2 Infection In Vivo BABL/c mice were administered i.p. with cobra venom factor (CVF, 30 µg/mouse, Quidel, San Diego, CA, USA), and 6 hours later, 1×10$^7$ CFU of S. aureus MW2 was injected with i.v. and then survival rate was monitored after intravenous injection of humanized antibody (h3F5H6)((25 mg/kg mouse).

Example 24: Analysis of the Effect of CpG-DNA in Mice from which Complement was Removed Against E. coli K1 Infection In Vivo BABL/c mice were injected with CpG-DNA (50 µg/mouse) by i.p. and after 7 days, CVF (30 µg/mouse) was administered to the mice by i.p. and the amount of complement (C3) in the serum was determined with an ELISA kit (Complement C3 mouse ELISA kit, Abcam, Cat. No. ab-157711) after 6 hours. BABL/c mice were injected with CpG-DNA (50 µg/mouse) by i.p. and after 7 days, CVF (30 µg/mouse) was administered by i.p. to the mice and injected with 5×10$^6$ CFU of E. coli K1 after 6 hours. he injected mice were observed for mortality or recovery for 2 days.

Example 25: Analysis of the Effect of Antibodies on E. coli K1 Infection In Vivo BABL/c mice were injected i.p. with 5×10$^6$ CFU of E. coli K1, followed by intravenous injection of normal human IgG and humanized antibody (h3F5H6) ((25 mg/kg mouse). Normal mouse IgG was purchased with Invitrogen. (Carlsbad, CA, USA). The survival rate was monitored 18 hours (E. coli K1) after antibody injection.

The results of the above examples are detailed below. Administration of CpG-DNA Enhances Survival of Mice and Facilitates Bacterial Clearance in Tissues after Infection with S. aureus MW2

We selected BALB/c mice as an animal model to prove anti-bacterial effect of CpG-DNA against infection of S. aureus MW2, and performed experiments according to the procedure depicted in FIG. 1A. BALB/c mice were first administered intraperitoneally (i.p.) with CpG-DNA 1826. After 7 days, the mice were injected intravenously (i.v.) with S. aureus MW2, and then survival rates were monitored for 7 days. Compared to the S. aureus MW2-infected mice without any treatment, survival rate of the mice pre-treated with CpG-DNA before bacterial infection increased up to 50% (10% vs 60%, FIG. 1B). For the assessment of bacterial infection in specific tissues, liver, lung, kidney, and spleen were excised 2 days after i.v. injection of S. aureus MW2. The tissues were homogenized, and the homogenates were incubated on the agar medium to count CFU. All the tested tissues were infected by bacteria, with the highest CFU in the kidney, and the bacterial loads in tissues were all decreased by the pre-treatment with CpG-DNA 1826 (FIG. 1C). Next, the histopathology of each tissue was observed. The abscess region appeared in the kidneys of mice after bacterial infection; however it was not detected when CpG-DNA 1826 was pretreated before infection (FIG. 1D). Therefore, we conclude that pre-administration of CpG-DNA to the mice leads to increased survival and enhanced bacterial clearance after S. aureus MW2 infection.

CpG-DNA Administration Protects and Modulates Cell Populations of Peritoneal Cavity, Spleen, and Bone Marrow after Infection of S. aureus MW2

To investigate the mechanisms involved in the protective effect of CpG-DNA against S. aureus MW2 infection, we analyzed cell populations with FACS in peritoneal cavity, spleen, and bone marrow from BALB/c mice according to the experimental schedule (FIG. 1A). Populations of lymphoid cells (B and T cells) and myeloid cells (macrophages, dendritic cells, and neutrophils) were differentially changed by CpG-DNA administration and S. aureus MW2 infection in different tissues (FIG. 2).

In peritoneal cavity, population ratio of myeloid cells and lymphoid cells was reversed by CpG-DNA (FIG. 2A). While myeloid cell population was decreased by CpG-DNA administration (61% of PBS control), population of lymphoid cells in peritoneal cavity was increased by CpG-DNA (160% of PBS control). Main population of myeloid cells was F4/80+ CD11b+ macrophages. Even though F4/80-CD11c+ dendritic cell population is very small, it was increased by CpG-DNA administration (3 times of PBS control). In the case of lymphoid cells, increase of T cell population including CD4+ and CD8+ T cells was prominent (4.6 times of PBS control) and total B cell population was similar. When we analyzed the B cell population in detail, B1 (CD23−) cell population was decreased and B2 (CD23+) cell population was slightly increased by CpG-DNA. When S. aureus MW2 was infected, all the population except neutrophils markedly decreased and pretreatment with CpG-DNA significantly recovered the cell population even though the population size is smaller than the untreated control (FIG. 2A).

In bone marrow, the myeloid cell population increased (150% of PBS control) and lymphoid population decreased (65% of PBS control) in response to CpG-DNA (FIG. 2B). The main population of myeloid cells was F4/80-Gr-1+ neutrophils. The major population of lymphoid cells was B cells, especially B1 cells. Differently from the peritoneal cavity, the ratio of B-1 and B-2 cell population was not changed by CpG-DNA. S. aureus MW2 infection induced marked decrease of all the population and the decrease was reversed by the pretreatment with CpG-DNA (FIG. 2B).

In spleen, there was no significant change of cell population induced by CpG-DNA administration (FIG. 2C). When S. aureus MW2 was infected, decrease of lymphoid cell population was observed (60% of PBS control). When CpG-DNA was pretreated before bacterial infection, the cell population was even larger than the PBS control. Compared to S. aureus MW2 infection alone, pre-treatment with CpG-DNA increased both of lymphoid and myeloid cell population more than 2 fold (FIG. 2C).

Based on these results, we conclude that infection of S. aureus MW2 induces decrease of total cell numbers in peritoneal cavity, bone marrow, and spleen and pretreatment of the mice with CpG-DNA commonly protects immune cells in these tissues. This phenomenon suggests that induced cell numbers in the tissues may enhance survival of infected mice. Most importantly, CpG-DNA changes the population of peritoneal cells in a direction to increase adaptive immune cells such as B2 cells, T cells, and macrophages (FIG. 2A). Therefore, we speculate that the peritoneal cavity cells may be the main regulator involved in the anti-bacterial effects of CpG-DNA in our experimental system.

Induction of Bacteria-Reactive Antibodies by Administration of CpG-DNA In Vivo and In Vitro We injected CpG-DNA 1826 i.p. and analyzed the supernatants of peritoneal cavity and serum at various time points to confirm the production of antibodies. Non-CpG-DNA 2041 was used as a negative control. The level of total IgG was significantly increased in peritoneal cavity supernatant on 3 and 7 days after administration of CpG-DNA 1826, however there was no meaningful change in serum (FIG. 3).

Considering that administration of CpG-DNA enhanced survival of *S. aureus* MW2 infected-mice, it is likely that some bacteria-reactive antibodies can be induced by CpG-DNA 1826 in peritoneal cavity. We harvested peritoneal cavity supernatant and serum from mice after administration of CpG-DNA 1826 and infection i.v. of *S. aureus* MW2 (FIG. 1A), and measured levels of total IgG and IgG isotypes reactive to *S. aureus* MW2 using plates coated with *S. aureus* MW2. CpG-DNA alone induced increase of reactive total IgG in the peritoneal cavity, but there was no significant change in sera. Infection of *S. aureus* MW2 decreased the production of reactive IgG both in peritoneal cavity and serum. However, pre-administration of CpG-DNA 1826 before bacterial infection induced significantly increased production of reactive IgG. IgG3 isotype was the most abundant in all the cases and the amount of *S. aureus* MW2-reactive IgG3 isotype was significantly increased in the CpG-DNA-treated group (FIG. 4A, B).

To further investigate the antibodies induced by CpG-DNA in mice, PBS or CpG-DNA 1826 was injected i.p. and supernatants of peritoneal cavity and serum were analyzed after 7 days. To determine whether the CpG-DNA-induced IgG can bind various species of Gram-positive bacteria, we performed ELISA assay using plates coated with *S. aureus, S. aureus* MW2, *S. epidermidis*, or *S. pyogenes*. Levels of each bacteria-reactive IgG were increased by the treatment of CpG-DNA 1826 in peritoneal cavity and serum (FIG. 4C, D). To investigate whether treatment of CpG-DNA activates TLR9 signaling pathway to produce bacteria-reactive antibodies, the same experiments were performed using BALB/c TLR9 –/– mice. In the peritoneal cavity and serum of TLR9–/– mice, there were no significant changes of bacteria-reactive antibodies induced by the treatment of CpG-DNA 1826 (FIG. 4E, F). Therefore, we conclude that CpG-DNA induced production of bacteria-reactive antibodies through TLR9.

To determine whether production of bacteria-reactive antibodies can be induced by CpG-DNA in vitro, immune cells of peritoneal cavity were harvested from the mice, stimulated in vitro with CpG-DNA 1826 and non-CpG-DNA 2041, and the cell culture supernatants were analyzed to measure the amounts of antibodies. As shown in FIG. 5A, general IgG production was significantly increased in response to CpG-DNA compared to PBS or non-CpG-DNA. When the mice were first primed with CpG-DNA in vivo and then the peritoneal cavity cells were stimulated in vitro, basal IgG production was higher than the control but additional effect of CpG-DNA treatment was very weak (FIG. 5A). To determine the binding capability of the antibodies secreted from the in vitro cultured-peritoneal cells, we measured amounts of bacteria-reactive IgG with four Gram-positive bacteria species. Production of bacteria-reactive IgG was significantly increased in response to CpG-DNA, but there were very few reactive antibodies found in response to PBS or non-CpG-DNA (FIG. 5B).

To investigate which B cells secrete bacteria-reactive antibodies in response to CpG-DNA, CpG-DNA 1826 was injected i.p. to the mice. On 9 days after injection of CpG-DNA 1826, we harvested immune cells of peritoneal cavity from the mice, sorted CD23–CD19+ B cells (B1 cells) and CD23+CD19+ (B2 cells) from peritoneal lymphocytes (FIG. 5C), and stimulated the cells with CpG-DNA 1826 in vitro. Both of B1 and B2 cells secreted increased amounts of IgG in response to CpG-DNA stimulation (FIG. 5D). However, the levels of IgG production by B cells in vitro were decreased when the mice was pre-treated with CpG-DNA before isolation of the peritoneal cavity cells, suggesting modulation of the B cell activity by CpG-DNA (FIG. 5D). The levels of each bacteria-reactive IgG, measured using Gram-positive bacteria-coated plates, suggested that production of bacteria-reactive IgG was increased by CpG-DNA stimulation in vitro and that priming with CpG-DNA in vivo modulates antibody-producing activity (FIG. 5E). Taken together, these results indicate that CpG-DNA-induced bacteria-reactive antibodies are produced in both B1 and B2 cells of peritoneal cavity in response to CpG-DNA.

Bacteria-Reactive Antibodies in Peritoneal Cavity Induced by CpG-DNA Enhance Phagocytosis We examined whether bacteria-reactive antibodies induced by CpG-DNA in the peritoneal cavity can enhance phagocytosis to resist bacterial infection. We purified the polyclonal antibodies in the peritoneal cavity supernatants of PBS-injected mice (FIG. 6A). The peritoneal cavity fluids were obtained from mice on 7 days after injection with CpG-DNA 1826 and then the polyclonal antibodies were purified (FIG. 6B). The amounts of IgG in the peritoneal cavity were increased about 2.5 fold by CpG-DNA 1826 administration compared to PBS control (7.5·g/mouse versus 3·g/mouse). Binding ability of the antibodies with *S. aureus* MW2 was also measured by ELISA. The results showed that the antibodies induced by CpG-DNA 1826 administration have higher binding ability with *S. aureus* MW2 than the antibodies from PBS-injected mice (FIG. 6C). Next, we determined efficacy of these antibodies in association with phagocytosis. FITC-labeled *S. aureus* MW2 was incubated with the purified antibodies and then phagocytosis assay was performed in the mouse macrophage cell line, RAW 264.7, by confocal microscopy (FIG. 6D, E). Phagocytosis index was increased with antibodies, and the antibodies from CpG-DNA 1826-injected peritoneal cavity were more effective than those from PBS-injected control (1.19 fold).

Selection of Hybridoma Clone Producing Bacteria-Reactive Monoclonal Antibody and Anti-Bacterial Effect of the Monoclonal Antibody on Phagocytosis Based on our results, we supposed that activated B cell clones induced by CpG-DNA may secrete anti-bacterial antibodies, and the antibodies would enhance phagocytosis via macrophages, dendritic cells, and neutrophils in the peritoneal cavity. To construct the B cell clone secreting CpG-DNA-induced bacteria-reactive antibody, mice were injected i.p. with CpG-DNA 1826. After 7 days, peritoneal cells were harvested and fused with SP2/0 myeloma cells. We isolated the hybridoma clone, named as m3F5H6, secreting the monoclonal antibody reactive to *S. aureus* MW2 (FIG. 7).

Cloning of Variable Domains of Bacterial-Reactive Monoclonal Antibodies

The cDNA sequences encoding the variable domains (VH and VL) of the heavy and light chains were cloned from hybridoma cells (m3F5H6) producing bacterial-reactive monoclonal antibodies using conventional heavy and light chain primers. Sequences identified by DNA sequencing are shown in FIG. 8. The sequences were analyzed for known sequences and homology using the IgBLAST program (Ye J, Ma N, Madden T L, Ostell J M. IgBLAST: Nucleic Acids Res. 2013; 41 (Web Server issue): W34-40).

The monoclonal antibody (m3F5H6 IgG) was purified from m3F5H6 clone-injected ascites and analyzed by SDS-PAGE (FIG. 9A). The isotype of 3F5H6 IgG was IgG2b (FIG. 9B), and binding ability of m3F5H6 IgG with several Gram-positive bacteria was confirmed by ELISA (FIG. 9C).

To examine the effect of m3F5H6 IgG on phagocytosis of RAW 264.7 cells, phagocytosis assay was performed using FITC-labeled S. aureus MW2 after incubation with PBS, mouse normal IgG or m3F5H6 IgG (FIG. 9D, E). We also investigated the effect of m3F5H6 IgG on phagocytosis of mouse peritoneal cavity cells (FIG. 9F, G). The results indicate that m3F5H6 IgG increases the activity of RAW264.7 cells and mouse peritoneal cavity cells to engulf S. aureus MW2 more effectively than mouse normal IgG (1.5~1.8 fold).

To directly investigate the effect of m3F5H6 IgG on phagocytosis in the mouse peritoneal cavity, mice were injected i.p. with m3F5H6 IgG after pre-incubation with FITC-labeled S. aureus MW2. cells. Then we analyzed the peritoneal cavity cells by flow cytometry to figure out the efficacy of phagocytic immune cells, such as macrophages, dendritic cells, and neutrophils (FIG. 9H). Compared with normal IgG control, m3F5H6 IgG more efficiently enhanced phagocytosis of macrophages and dendritic cells in the peritoneal cavity. However, there was no effect on the phagocytosis of neutrophils. These results suggest that m3F5H6 IgG is an effective phagocytosis mediator in mouse peritoneal cells and that phagocytic immune cells can be related to the anti-bacterial effect of CpG-induced antibodies.

Bacterial-Reactivity of Monoclonal Antibody (m3F5H6 IgG)

The binding ability of the monoclonal antibody (m3F5H6 IgG) to Gram-positive bacteria was confirmed by ELISA (FIG. 9C). Further, Gram-negative bacteria of monoclonal antibody (m3F5H6 IgG) (FIG. 10A). And the binding force to the intracellular parasitic bacteria (FIG. 10B) was confirmed by ELISA.

Bacteria-Reactive Monoclonal Antibody (m3F5H6 IgG) from CpG-DNA Stimulated-Peritoneal B Cells has Therapeutic Effects Against Infection of S. aureus MW2

To prove anti-bacterial effect of m3F5H6 IgG against infection of S. aureus MW2 in mice, BALB/c mice were infected with S. aureus MW2, subsequently administered i.v. with PBS, normal IgG, and m3F5H6 IgG, and then mortality, infection in tissues, and histopathology were observed according to the experimental schedule (FIG. 11A). All the mice infected with S. aureus MW2 without antibody died on days 5 after infection, but 30% of the normal IgG injected-mice and 70% of m3F5H6 IgG injected-mice survived until days 7 after infection (FIG. 11B).

To investigate the infection of S. aureus MW2 in specific tissues, liver, lung, kidney and spleen were prepared 2 days after the infection and CFU assay was executed. We observed decrease of bacterial loads in the tissues, especially in the kidneys, by administration of m3F5H6 IgG (FIG. 11C). The histopathology of the tissues was also monitored 2 days after infection. Bacterial burdens were found only in the kidney, and smaller bacterial burdens were detected in antibody injected-mice, compared to only S. aureus MW2 infected-mice (FIG. 11D). On 30 days after infection of S. aureus MW2, we examined histopathology of liver, lung, kidney, and spleen. No bacterial burden and many inflammatory immune cells were detected in kidney of antibody-injected mice (FIG. 11E). Taken these data all together, we noted that administration of CpG-DNA-induced antibody also lead to the increased survival and enhanced bacterial clearance in the S. aureus MW2-infected mice, with higher efficacy than normal IgG.

Production and Characterization of Bacterial-Reactive Humanized Antibodies

For the clinical application of monoclonal antibodies, humanization of the antibodies to reduce immunogenicity in humans must be performed. Therefore, the present inventors used the immunoglobulin variable domain sequence of the obtained monoclonal antibody m3F5H6 using the IgBLAST program (Ye J, Ma N, Madden T L, Ostell J M. IgBLAST: Nucleic Acids Res. 2013; 41 (Web Server issue): W34-40, and found that the variable domain subtype belongs to mouse VH1-Vk1. For the humanization of m3F5H6 mAb, the inventors confirmed that the VH1-Vk1 skeleton is most commonly observed in the human germ line repertoire (Caravella J A, Wang D, Glaser S M, Lugovskoy A. Curr Comput Aided Drug) Des. 2010; 6(2):128-138). In this case, the present inventors grafted some framework sequences of the human VH1-Vk1 framework with the Samalizumab framework and the CDR regions by a conventionally established method (Kabat E A, Wu T T. J Immunol. 1991; 147(5):1709-1719). Structures derived from m3F5H6 and humanized monoclonal antibody (h3F5H6) were modeled and compared, and they were not identical to each other, but showed that they were similar (FIG. 12).

The present inventors produced a recombinant humanized monoclonal antibody (h3F5H6) using HEK 293F cells (FIG. 13) and evaluated its reactivity (FIG. 14, FIG. 15). Based on ELISA, it was confirmed that the humanized antibodies react specifically with Gram(+) bacteria (S. aureus, S. aureus MW2, S. epidermidis, S, pyogenes) and Gram(−) bacteria (A. baumannii, E. coli K1, P. aeruginosa, K. pneumoniae 11418, K. pneumoniae 40145, K. pneumoniae 41293) (FIG. 14) and intracellular parasitic bacteria (L. monocytogenes, S. typhimurium) (FIG. 15).

Bacteria-Reactive Humanized Antibody (h3F5H6 IgG) has Therapeutic Effects Against Infection of S. aureus MW2

To prove anti-bacterial effect of h3F5H6 IgG against infection of S. aureus MW2 in mice, BALB/c mice were infected with S. aureus MW2, subsequently administered i.v. with PBS, normal human IgG, and h3F5H6 IgG, and then mortality, and histopathology were observed according to the experimental schedule (FIG. 16A).

All the mice infected with S. aureus MW2 without antibody died on days 5 after infection, but 10% of the normal IgG injected-mice and 30% of h3F5H6 IgG injected-mice survived until days 7 after infection (FIG. 16B). The histopathology of the tissues was also monitored 2 days after infection. Bacterial burdens were found only in the kidney, and smaller bacterial burdens were detected in antibody injected-mice, compared to only S. aureus MW2 infected-mice (FIG. 16C).

BABL/c mice were injected with cobra venom factor (CVF, 30 μg/mouse) by i.p. and after 6 hours $1\times10^7$ CFU of S. aureus MW2 were injected i.v., and humanized antibody (h3F5H6) ((25 mg/kg mouse) was monitored after intravenous injection. All mice administered with CFV infected with S. aureus MW2 and not administered antibody died after 4 days, but mice injected with 20% h3F5H6 IgG survived until 7 days after infection (FIG. 17). It was shown that complement-independently the h3F5H6 IgG antibody inhibited S. aureus MW2 infection.

Administration of CpG-DNA Promotes Removal of Bacteria from Tissues after Infection with *E. coli* K1 and Increases Survival of Mice.

The present inventors were selected as an animal model to demonstrate the antibacterial effect of *E. coli* K1 against infection, and experiments were performed according to the method described in FIG. 18A. First, BALB/c mice were administered intraperitoneally (i.p.) CpG-DNA 1826 and 7 days later, the mice were injected by intraperitoneal (i.p.) with *E. coli* K1, and the survival rate was monitored for 2 days. Compared to the *E. coli* K1-injected mice without any treatment, the survival rate of mice pretreated with CpG-DNA before bacterial infection was increased to 100% (FIG. 18B).

To prove anti-bacterial effect of h3F5H6 IgG against infection of *E. coli* K1 in mice, BALB/c mice were infected i.p. with *E. coli* K1, subsequently administered i.v. with PBS, normal human IgG, and h3F5H6 IgG, and then mortality was observed. 50% of mice infected with *E. coli* K1 without antibody died on 8 h after infection, but 80% of h3F5H6 IgG injected-mice survived until 18 h after infection (FIG. 15). Taken these data all together, we noted that administration of humanized bacteria-reactive antibody (h3F5H6 IgG) also lead to the increased survival and enhanced bacterial clearance in the *S. aureus* MW2- or *E. coli* K1-infected mice, with higher efficacy than normal IgG.

For the evaluation of bacterial infection in specific tissues, liver, lung, kidney and spleen were examined by i.p. of *E. coli* K1. One day after injection, the tissue was cut out to homogenize the tissue, and the homogenate was cultured in an agar medium to remove it, and CFU was counted. All the tested tissues and blood and abdominal cavity were infected by bacteria, and the bacterial load in the tissues was all reduced by pretreatment with CpG-DNA 1826 (FIG. 18C).

Next, the histopathology of each tissue was observed. After bacterial infection, no abscess site was detected in the tissue of the mouse (FIG. 18D). Therefore, the present inventors concluded that the pretreatment of CpG-DNA in mice promotes the removal of bacteria and increases the survival rate after *E. coli* K1 infection.

To demonstrate that the antimicrobial effect of CpG-DNA against infection of *E. coli* K1 in mice is complement-independent, BALB/c mice were administered intraperitoneally (i.p.) CpG-DNA 1826 and after 7 days, the mouse was injected with CVF intraperitoneally (i.p.), and the amount of complement (C3) in the serum was measured (FIG. 19A). After administration of CVF, it was confirmed that all of the complement was reduced in serum (FIG. 19B). Seven days after the administration of CpG-DNA 1826, the mice were injected with intraperitoneal (i.p.) CVF, and then 6 hours later, *E. coli* K1 was infected with i.p. (FIG. 19C). The survival rate of mice pretreated with CpG-DNA before bacterial infection increased by 20% (FIG. 19D). Therefore, the present inventors concluded that the pretreatment of CpG-DNA in mice promotes complement-independent removal of bacteria and increases survival rate after *E. coli* K1 infection.

Bacterial-Reactive Humanized Antibody (h3F5H6 IgG) has a Therapeutic Effect Against Infection of *E. coli* K1

To demonstrate the antimicrobial effect of h3F5H6 IgG against *E. coli* K1 infection in mice, BALB/c mouse mice were infected with *E. coli* K1 i.p., and then PBS, normal human IgG, and h3F5H6 IgG were administered i.v. and observed the death rate. It was also confirmed that administration of the humanized bacteria-reactive antibody (h3F5H6 IgG) also increased the survival rate and higher bacterial clearance in *E. coli* K1-infected mice than in normal IgG (FIG. 20).

The invention claimed is:

1. A monoclonal antibody specifically binding to *S. aureus* NW2, said monoclonal antibody comprising:

a heavy chain comprising a complementarity determining region 1 (CDR 1) amino acid sequence consisting of the sequence of SEQ ID NO: 1, a CDR2 consisting of the sequence of SEQ ID NO: 2 and a CDR 3 consisting of the sequence of SEQ ID NO: 3; and a light chain comprising CDR1 amino acid sequence consisting of the sequence of SEQ ID NO: 4, a CDR2 consisting of the sequence of SEQ ID NO: 5 and a CDR 3 consisting of the sequence of SEQ ID NO: 6.

2. The monoclonal antibody of claim 1, wherein said monoclonal antibody comprises a heavy chain comprising an amino acid sequence consisting of the sequence of SEQ ID NO: 7, or the sequence of SEQ ID NO: 15; and a light chain comprising an amino acid sequence consisting of the sequence of SEQ ID NO: 8, or the sequence of SEQ ID NO: 16.

3. An antimicrobial composition comprising a monoclonal antibody specifically binding to *S. aureus* NW 2, said monoclonal antibody comprising:

a heavy chain comprising a complementarity determining region 1 (CDR 1) amino acid sequence consisting of the sequence of SEQ ID NO: 1, a CDR2 consisting of the sequence of SEQ ID NO: 2 and a CDR 3 consisting of the sequence of SEQ ID NO: 3; and a light chain comprising CDR1 amino acid sequence consisting of the sequence of SEQ ID NO: 4, a CDR2 consisting of the sequence of SEO ID NO: 5 and a CDR 3 consisting of the sequence of SEQ ID NO: 6 as an active ingredient.

4. The composition of claim 3, wherein the composition has antibacterial activity against Gram-positive bacteria, Gram-negative bacteria, intracellular parasitic bacteria, or drug-resistant bacteria.

5. The composition of claim 3, wherein the composition has antimicrobial activity against methicillin-resistant *Staphylococcus aureus* (MRSA), *Staphylococcus aureus, Listeria, Salmonella*, or *E. coli*.

* * * * *

SEQUENCE LISTING

```
<160> NUMBER OF SEQ ID NOS: 16

<210> SEQ ID NO 1
<211> LENGTH: 10
<212> TYPE: PRT
<213> ORGANISM: Artificial Sequence
<220> FEATURE:
<223> OTHER INFORMATION: CDR1

<400> SEQUENCE: 1

Gly Tyr Ser Phe Thr Gly Tyr Tyr Met His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: CDR2

<400> SEQUENCE: 2

Arg Ile Asn Pro Tyr Asn Gly Ala Thr Ser Tyr Asn Gln Asn Phe Lys
1               5                   10                  15

Asp

<210> SEQ ID NO 3
<211> LENGTH: 9
<212> TYPE: PRT
<213> ORGANISM: Artificial Sequence
<220> FEATURE:
```

```
<223> OTHER INFORMATION: CDR3

<400> SEQUENCE: 3

Asp Tyr Gly Ser Ser Tyr Phe Asp Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: CDR1

<400> SEQUENCE: 4

Arg Ala Ser Gln Ser Ile Ser Asp Tyr Leu His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: CDR2

<400> SEQUENCE: 5

Tyr Ala Ser Gln Ser Ile Ser
1               5

<210> SEQ ID NO 6
<211> LENGTH: 9
<212> TYPE: PRT
<213> ORGANISM: Artificial Sequence
<220> FEATURE:
<223> OTHER INFORMATION: CDR3

<400> SEQUENCE: 6

Gln Asn Gly His Ser Phe Pro Leu Thr
1               5

<210> SEQ ID NO 7
<211> LENGTH: 118
<212> TYPE: PRT
<213> ORGANISM: Artificial Sequence
<220> FEATURE:
<223> OTHER INFORMATION: VH

<400> SEQUENCE: 7

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
                20                  25                  30

Tyr Met His Trp Val Lys Gln Ser His Val Lys Ser Leu Glu Trp Ile
            35                  40                  45

Gly Arg Ile Asn Pro Tyr Asn Gly Ala Thr Ser Tyr Asn Gln Asn Phe
        50                  55                  60

Lys Asp Lys Ala Ser Leu Thr Val Asp Lys Ser Ser Thr Ala Tyr
65                  70                  75                  80

Met Glu Leu His Ser Leu Thr Ser Glu Asp Ser Ala Val Tyr Tyr Cys
                85                  90                  95

Ala Gly Asp Tyr Gly Ser Ser Tyr Phe Asp Tyr Trp Gly Gln Gly Thr
                100                 105                 110

Thr Leu Thr Val Ser Ser
            115
```

<210> SEQ ID NO 8
<211> LENGTH: 108
<212> TYPE: PRT
<213> ORGANISM: Artificial Sequence
<220> FEATURE:
<223> OTHER INFORMATION: VL

<400> SEQUENCE: 8

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Arg
            100                 105

<210> SEQ ID NO 9
<211> LENGTH: 20
<212> TYPE: DNA
<213> ORGANISM: Artificial Sequence
<220> FEATURE:
<223> OTHER INFORMATION: CpG-DNA

<400> SEQUENCE: 9
tccatgacgt tcctgacgtt                                           20

<210> SEQ ID NO 10
<211> LENGTH: 24
<212> TYPE: DNA
<213> ORGANISM: Artificial Sequence
<220> FEATURE:
<223> OTHER INFORMATION: Non-CpG-DNA

<400> SEQUENCE: 10
ctggtctttc tggttttttt ctgg                                      24

<210> SEQ ID NO 11
<211> LENGTH: 33
<212> TYPE: DNA
<213> ORGANISM: Artificial Sequence
<220> FEATURE:
<223> OTHER INFORMATION: primer

<400> SEQUENCE: 11
ggaagatcta ggggccagtg gatagactga tgg                            33

<210> SEQ ID NO 12
<211> LENGTH: 35
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(18)
<223> OTHER INFORMATION: n is a, c, g, or t

```
<400> SEQUENCE: 12
cttccggaat tcsargtnma gctgsagsag tcwgg                                    35

<210> SEQ ID NO 13
<211> LENGTH: 30
<212> TYPE: DNA
<213> ORGANISM: Artificial Sequence
<220> FEATURE:
<223> OTHER INFORMATION: primer

<400> SEQUENCE: 13
ggtgcatgcg gatacagttg gtgcagcatc                                         30

<210> SEQ ID NO 14
<211> LENGTH: 32
<212> TYPE: DNA
<213> ORGANISM: Artificial Sequence
<220> FEATURE:
<223> OTHER INFORMATION: primer

<400> SEQUENCE: 14
gggagctcga yattgtgmts acmcarwctm ca                                      32

<210> SEQ ID NO 15
<211> LENGTH: 118
<212> TYPE: PRT
<213> ORGANISM: Artificial Sequence
<220> FEATURE:
<223> OTHER INFORMATION: VH

<400> SEQUENCE: 15
```

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Arg Gln Asn His Val Lys Gly Leu Glu Trp Ile
        35                  40                  45

Gly Arg Ile Asn Pro Tyr Asn Gly Ala Thr Ser Tyr Asn Gln Asn Phe
    50                  55                  60

Lys Asp Arg Ala Thr Leu Thr Val Asp Lys Ser Thr Thr Thr Ala Tyr
65                  70                  75                  80

Met Glu Leu His Ser Leu Thr Ser Glu Asp Thr Ala Val Tyr Tyr Cys
                85                  90                  95

Ala Gly Asp Tyr Gly Ser Ser Tyr Phe Asp Tyr Trp Gly Gln Gly Thr
            100                 105                 110

Thr Leu Thr Val Ser Ser
        115

```
<210> SEQ ID NO 16
<211> LENGTH: 108
<212> TYPE: PRT
<213> ORGANISM: Artificial Sequence
<220> FEATURE:
<223> OTHER INFORMATION: VL

<400> SEQUENCE: 16
```

Asp Ile Val Met Thr Gln Ser Pro Ser Ser Leu Ser Ala Ser Pro Gly
1               5                   10                  15

Asp Arg Val Thr Ile Thr Cys Arg Ala Ser Gln Ser Ile Ser Asp Tyr
            20                  25                  30

-continued

```
Leu His Trp Tyr Gln Gln Lys Ser His Lys Ala Pro Lys Leu Leu Ile
        35                  40                  45

Lys Tyr Ala Ser Gln Ser Ile Ser Gly Val Pro Ser Arg Phe Ser Gly
 50                  55                  60

Ser Gly Ser Gly Ser Asp Tyr Thr Leu Thr Ile Ser Ser Leu Gln Pro
 65              70                  75                  80

Glu Asp Phe Ala Val Tyr Tyr Cys Gln Asn Gly His Ser Phe Pro Leu
                85                  90                  95

Thr Phe Gly Gly Gly Thr Lys Leu Glu Ile Lys Arg
            100                 105
```